(12) United States Patent
Kobayashi et al.

(10) Patent No.: US 6,815,191 B1
(45) Date of Patent: Nov. 9, 2004

(54) ENDO-β-N-ACETYLGLUCOSAMINIDASE GENE

(75) Inventors: Kazuo Kobayashi, Yokohama (JP); Makoto Takeuchi, deceased, late of Yokohama (JP); by Yoriko Takeuchi, legal representative, Yokohama (JP); Akihiko Iwamatsu, Yokohama (JP); Kenji Yamamoto, Otsu (JP); Hidehiko Kumagai, Otsu (JP); Satoshi Yoshida, Yokohama (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/700,993

(22) PCT Filed: May 20, 1999

(86) PCT No.: PCT/JP99/02644

§ 371 (c)(1),
(2), (4) Date: Jul. 20, 2001

(87) PCT Pub. No.: WO99/61591

PCT Pub. Date: Dec. 2, 1999

(30) Foreign Application Priority Data

May 22, 1998 (JP) ............................................ 10-141717

(51) Int. Cl.⁷ ............................. C12N 9/26; C12N 1/14; C07H 21/04
(52) U.S. Cl. .................... 435/201; 435/203; 435/320.1; 435/252.3; 435/254.11; 536/23.2; 536/23.7; 536/23.74
(58) Field of Search ............................. 435/201, 320.1, 435/252.3, 254.8, 203, 254.11; 536/23.2, 23.7

(56) References Cited

FOREIGN PATENT DOCUMENTS

| EP | A2 0 769 550 | 4/1997 |
|---|---|---|
| EP | A1 0 905 232 | 3/1999 |
| JP | 1-309685 | 12/1989 |
| JP | 7-59587 | 3/1995 |
| JP | 11-89574 | 4/1999 |

OTHER PUBLICATIONS

Takegawa et al. (1997) Arch Biochem Biophys 338:22–28, abstract.*

Katsuji et al.; "Transglycosylation 1–9 of intact sialo complex–type oligosaccharides to the N–acetylglucosamine moieties of glycopeptides by Mucor hiemalis endo–β–N–acetylglucosaminidase." Carbohydrate Research, vol. 292, 1996 pp. 61–70.

Oshida et al. "A *Staphylococcos aureus* autolysin that has an N–acetylmuramoyl–L–alanine amidase domain and an endo–β–N–acetylglucosaminidase domain: Cloning, sequence analysis, and characterization". Proceedings of the National Academy of Sciences of USA, National Academy of Science. Washington, US, vol. 92, 1995, pp. 285–289.

Yamamoto et al. "Transglycosylation Activity of Mucor hiemalis Endo–β–N–Acetyl–glucosaminidase Which Transfers Complex Oligosaccharides to the N–Acetylglucosamine Moieties of Peptides". Biochemical and Biophysical Research Communications, vol. 203, No. 1, 1994, pp. 244–252.

Anthony L. Tarentino et al., "Purification and Properties of and Endo–β–N–acetylglucosaminidase from *Streptomyces griseus*.", The Journal of Biological chemistry, vol. 249, No. 3, pp. 811–817, 1974.

Kaoru Takegawa et al., "Complete amino acid sequence of endo–β–N–acetylglucosaminidase from *Flavobacterium* sp.", European Journal of Biochemistry, vol. 202, pp. 175–180, 1991.

Kaoru Takegawa et al., "Induction and Purification of Endo–β–N–acetylglucosaminidase from *Arthrobacter protophormiae* Grown in Ovalbumin.", Applied and environmental Microbiology, pp. 3107–3112, 1989.

Setsu Kadowaki et al., "Purification and Characterization of a Novel Fungal Endo–β–N–acetylglucosaminidase Acting on Compled Oligosaccharides of Glycoproteins.", (Reprint) Agricultural and Biological chemistry, vol. 54, No. 1, pp. 97–106, 1990.

Budapest Treaty on the International Recognition of the Deposit of Microorganisms for the Purposes of Patent Procedure, Acession No. FERM–BP–6335, Apr. 1998.

* cited by examiner

*Primary Examiner*—Rebecca E. Prouty
*Assistant Examiner*—David J Steadman
(74) *Attorney, Agent, or Firm*—Foley & Lardner, LLP

(57) ABSTRACT

An endo-β-N-acetylglucosaminidase gene encoding the following protein (a) or (b): (a) a protein comprising the amino acid sequence represented by SEQ ID NO: 3; and (b) a protein comprising an amino acid sequence derived from the amino acid sequence represented by SEQ ID NO: 3 by deletion, substitution, or addition of at least one amino acid and having the activity of endo-β-N-acetylglucosaminidase.

12 Claims, 9 Drawing Sheets

Purification Result for Endo-β-N-acetylglucosaminidase (15-25% gradient SDS-PAGE)

Lane 1: Purified endo-β-N-acetylglucosaminidase from *Mucor hiemalis*
Lane 2: Molecular weight markers

FIG. 3

```
         10         20         30         40         50         60
  GTCCACCCAC GCGTCCGCGG ACGCGTGGGC GGACCCGTCG GCGGACGCGT GGGTTTTATT 70         80         90        100        110        120
  TTACATAAAT ATGCCTTCAC TTCAATTGCA ACCTGATGAC AAACTAGCAC CTGTTTCTTT 130        140        150        160        170        180
  TGCACTTAAG TCTATGAATG AGTTGAGGGA CTGGACGCCA GACGAAAAGA TAAAGTTTAA 190        200        210        220        230        240
  CGTTTCAAGC GTGGCACTAC AGCCTCGTGT GAAAAACGCC CTGAAACCTC AATTATTGTT 250        260        270        280        290        300
  AACTCATGAT ATGGCAGGAG GATATAAAGA AGATAAAAAT ATTCAAGGAA ACAATTATAA 310        320        330        340        350        360
  AGACATTTAT AACATTCAAT ATTGGCATTT AGCTGATACT TTTGTATATT TCTCTCATGA 370        380        390        400        410        420
  GCGAGTTAGC ATTCCTCCAG TCAATTGGAC AAATGCTTGT CATAGAAATG GTGTAAAGTG 430        440        450        460        470        480
  TTTAGGTACT TTTTTAGTAG AAGGAAATAA CCAAATGCAT GAAATGAAG CCTTGCTTCA 490        500        510        520        530        540
  CGGTCCACCT TTACTTAATA ACACTGACGA CCCTATGAGA TTATGGAGTC CGTATTATGC 550        560        570        580        590        600
  AGACCAATTA GTTGCTATTG CTAAACACTA TGGTTTTGAT GGCTGGTTGT TCAATATTGA 610        620        630        640        650        660
  ATGCGAATTC TTTCCTTTTC CTACAAATCC AAAATTCAAA GCTGAAGAGT TGGCAAAGTT 670        680        690        700        710        720
  TCTACACTAT TTTAAGGAAA AATTGCATAA CGAAATACCT GGATCTCAAC TCATTTGGTA 730        740        750        760        770        780
  CGACAGCATG ACAAATGAAG GAGAAATCCA CTGGCAGAAC CAGCTCACAT GGAAAAATGA 790        800        810        820        830        840
  GTTATTTTTT AAAAACACGG ATGGTATTTT TTTGAATTAT TGGTGGAAAA AAGAATACCC 850        860        870        880        890        900
  TGAAATGGCG CGTAGAGTAG CTGAAGGAAT AGGTAGATCA GGTTTAGAAG TTTATTTTGG 910        920        930        940        950        960
  TACAGATGTA TGGGGAAGGC ATACTTATGG TGGCGGTGGT TTCAAATCAT ATAAGGGTGT 970        980        990       1000       1010       1020
  AAAAACTGCC TACTCTGCAA TGACATCTTC TGCATTATTT GGTATGGCAT GGACATACGA 1030       1040       1050       1060       1070       1080
  GCATTTCGAA AAGTCTGAAT TTGAAAAGAT GGATCGTTTG TTTTGGTGTG GTGGTAAATA 1090       1100       1110       1120       1130       1140
  CTCTGACTAT CCTCCCCCAC CTCCTAAAAA CCCAGATGAC GAAAAAGAAG TAGAAAGCGA 1150       1160       1170       1180       1190       1200
  TGATAGTGAA GATGAGCTCA TGTACGGACA CAAGAAAGGT ATTGCTGACA CGGTAGAATC 1210       1220       1230       1240       1250       1260
  TATTCCTGTA CCAGGAACAG ATTGGTTTGT TACCAATTTT GATAGGGGGT TTGGAAATAG 1270       1280       1290       1300       1310       1320
  GTTTTATTAT AGAGGAAAGA GATTACTTTC TCAGCCTTGG TCCCATTTAT CGCATCAAGC 1330       1340       1350       1360       1370       1380
  TATTCTCCCC AATAAAAGCT ATCGAAATCC AGAGATTTAT CCCACTGATC AAAACATTAA
```

Entire nucleotide sequence of the fragment inserted into the Sal I-Not I sites of pZL-Endo including the full-length novel endo-$\beta$-N-acetylglucosaminidase gene

FIG. 4

```
         1390       1400       1410       1420       1430       1440
    AATCACTAGT TCTCTCGATT GCGATCATGG AGCTTTTCTT GGTGGAACCT CGCTTATTAT 1450       1460       1470       1480       1490       1500
    CAAAGGCCAA CGTTTCAATC ATAGAGAATC GCATGATGTT GAAACTGAAA TTAGTATACC 1510       1520       1530       1540       1550       1560
    TCTGTATAAG CTTTCATTAG ATGCTAGTAA AGGATGCTCA TTGCGTTATA TTTATAGAAC 1570       1580       1590       1600       1610       1620
    TTTGTTGATG AAAGATGTAA AGTTGACAGT AGCATGTCAC TTTTCGTTAA AAACAAACGA 1630       1640       1650       1660       1670       1680
    CTCAGTTAAT TTCTTCAAGG TATGGCAGCC AGATGAAAAT TTCTCTTTTG AATATGATGA 1690       1700       1710       1720       1730       1740
    TGGAATGAGA GCCACTGTTA CAACTGAAAA TTCTACCGAA AGCAGATGCT TTTTATTACG 1750       1760       1770       1780       1790       1800
    TACAACAGAA GAAGATACAG GAGAAAATGA TTGGATAACA AAAACTATTA ATGTGCCTGC 1810       1820       1830       1840       1850       1860
    TGTTCCAGAA GGAAGTCAAT TATACATTAC AAGACTTGAA GTGAGCGTAG TATTAGATAC 1870       1880       1890       1900       1910       1920
    AGCTGGTTTA GTAGGTCTTG TTAATCAAGT TATTGCTTGC TTGGGATATA TTAGCATCAT 1930       1940       1950       1960       1970       1980
    ACCAACTATA AATTCTGGAA TAAAAACAGA TTCATCACGC ATTATTCAGG ATCTCTTTTG 1990       2000       2010       2020       2030       2040
    GAAAGATCAG AAATATACCA AAATCGGAAA AGAAAGTTTA GACGACATAG CTCAAGAAGA 2050       2060       2070       2080       2090       2100
    AGTTCATAGA TATTATGAA CATTGAACTG GGAAAACACA GCAAATGTAG TAAACGCTTG 2110       2120       2130       2140       2150       2160
    GGAGGAAATA GATTACTACA ACGTTTTTTA CAAAGAAAGT GACGACTCTG CAACTCGCAT 2170       2180       2190       2200       2210       2220
    CTTTTTAGGA ACAGCCATTCT GTAATCAATT TCGTGTATCT GGTTTAGATA TTATTTTATC 2230       2240       2250       2260       2270       2280
    TAAGCTACCA AAGATAGTTA TTGAAGCTGT TAACAAAGAA GGATACATCT CTTCAAGTGG 2290       2300       2310       2320       2330       2340
    TAGCATAGAT TTGTCATTAA ACTAGGACTT GAAATAAAAT ATTATGATAA AGAAAAAAAA 2350       2360       2370       2380       2390       2400
    AAAAAAAAAA AAAAAAAAAG GGCGGCCGC.  .. ..  .  ..   .........  ..  ...  ..
```

Entire nucleotide sequence of the fragment inserted into the Sal I-Not I sites of pZL-Endo including the full-length novel endo-$\beta$-N-acetylglucosaminidase gene (Continued)

FIG. 5

```
                9                18               27               36               45             54
5' ATG CCT TCA CTT CAA TTG CAA CCT GAT GAC AAA CTA GCA CCT GTT TCT TTT GCA
    M   P   S   L   Q   L   Q   P   D   D   K   L   A   P   V   S   F   A 63               72               81               90               99            108
   CTT AAG TCT ATG AAT GAG TTG AGG GAC TGG ACG CCA GAC GAA AAG ATA AAG TTT
    L   K   S   M   N   E   L   R   D   W   T   P   D   E   K   I   K   F 117              126              135              144              153            162
   AAC GTT TCA AGC GTG GCA CTA CAG CCT CGT GTG AAA AAC GCC CTG AAA CCT CAA
    N   V   S   S   V   A   L   Q   P   R   V   K   N   A   L   K   P   Q 171              180              189              198              207            216
   TTA TTG TTA ACT CAT GAT ATG GCA GGA GGA TAT AAA GAA GAT AAA AAT ATT CAA
    L   L   L   T   H   D   M   A   G   G   Y   K   E   D   K   N   I   Q 225              234              243              252              261            270
   GGA AAC AAT TAT AAA GAC ATT TAT AAC ATT CAA TAT TGG CAT TTA GCT GAT ACT
    G   N   N   Y   K   D   I   Y   N   I   Q   Y   W   H   L   A   D   T 279              288              297              306              315            324
   TTT GTA TAT TTC TCT CAT GAG CGA GTT AGC ATT CCT CCA GTC AAT TGG ACA AAT
    F   V   Y   F   S   H   E   R   V   S   I   P   P   V   N   W   T   N 333              342              351              360              369            378
   GCT TGT CAT ACA AAT GGT GTA AAG TGT TTA GGT ACT TTT TTA GTA GAA GGA AAT
    A   C   H   R   N   G   V   K   C   L   G   T   F   L   V   E   G   N 387              396              405              414              423            432
   AAC CAA ATG CAT GAA ATG GAA GCC TTG CTT CAC GGT CCA CCT TTA CTT AAT AAC
    N   Q   M   H   E   M   E   A   L   L   H   G   P   P   L   L   N   N 441              450              459              468              477            486
   ACT GAC GAC CCT ATG AGA TTA TGG AGT CCG TAT TAT GCA GAC CAA TTA GTT GCT
    T   D   D   P   M   R   L   W   S   P   Y   Y   A   D   Q   L   V   A 495              504              513              522              531            540
   ATT GCT AAA CAC TAT GGT TTT GAT GGC TGG TTG TTC AAT ATT GAA TGC GAA TTC
    I   A   K   H   Y   G   F   D   G   W   L   F   N   I   E   C   E   F 549              558              567              576              585            594
   TTT CCT TTT CCT ACA AAT CCA AAA TTC AAA GCT GAA GAG TTG GCA AAG TTT CTA
    F   P   F   P   T   N   P   K   F   K   A   E   E   L   A   K   F   L 603              612              621              630              639            648
   CAC TAT TTT AAG GAA AAA TTG CAT AAC GAA ATA CCT GGA TCT CAA CTC ATT TGG
    H   Y   F   K   E   K   L   H   N   E   I   P   G   S   Q   L   I   W 657              666              675              684              693            702
   TAC GAC AGC ATG ACA AAT GAA GGA GAA ATC CAC TGG CAG AAC CAG CTC ACA TGG
    Y   D   S   M   T   N   E   G   E   I   H   W   Q   N   Q   L   T   W
```

Amino acid sequence deduced from the novel Endo-β-N-acetylglucosaminidase gene, and the nucleotide sequence of the DNA encoding this amino acid sequence.

FIG. 6

```
         711           720           729           738           747           756
AAA AAT GAG TTA TTT TTT AAA AAC ACG GAT GGT ATT TTT TTG AAT TAT TGG TGG
 K   N   E   L   F   F   K   N   T   D   G   I   F   L   N   Y   W   W 765           774           783           792           801           810
AAA AAA GAA TAC CCT GAA ATG GCG CGT AGA GTA GCT GAA GGA ATA GGT AGA TCA
 K   K   E   Y   P   E   M   A   R   R   V   A   E   G   I   G   R   S 819           828           837           846           855           864
GGT TTA GAA GTT TAT TTT GGT ACA GAT GTA TGG GGA ACG CAT ACT TAT GGT GGC
 G   L   E   V   Y   F   G   T   D   V   W   G   R   H   T   Y   G   G 873           882           891           900           909           918
GGT GGT TTC AAA TCA TAT AAG GGT GTA AAA ACT GCC TAC TCT GCA ATG ACA TCT
 G   G   F   K   S   Y   K   G   V   K   T   A   Y   S   A   M   T   S 927           936           945           954           963           972
TCT GCA TTA TTT GGT ATG GCA TGG ACA TAC GAG CAT TTC GAA AAG TCT GAA TTT
 S   A   L   F   G   M   A   W   T   Y   E   H   F   E   K   S   E   F 981           990           999          1008          1017          1026
GAA AAG ATG GAT CGT TTG TTT TGG TGT GGT GGT AAA TAC TCT GAC TAT CCT CCC
 E   K   M   D   R   L   F   W   C   G   G   K   Y   S   D   Y   P   P 1035          1044          1053          1062          1071          1080
CCA CCT CCT AAA AAC CCA GAT GAC GAA AAA GAA GTA GAA AGC GAT GAT AGT GAA
 P   P   P   K   N   P   D   D   E   K   E   V   E   S   D   D   S   E 1089          1098          1107          1116          1125          1134
GAT GAG CTC ATG TAC GGA CAC AAG AAA GGT ATT GCT GAC ACG GTA GAA TCT ATT
 D   E   L   M   Y   G   H   K   K   G   I   A   D   T   V   E   S   I 1143          1152          1161          1170          1179          1188
CCT GTA CCA GGA ACA GAT TGG TTT GTT ACC AAT TTT GAT AGG GGG TTT GGA AAT
 P   V   P   G   T   D   W   F   V   T   N   F   D   R   G   F   G   N 1197          1206          1215          1224          1233          1242
AGG TTT TAT TAT AGA GGA AAG AGA TTA CTT TCT CAG CCT TGG TCC CAT TTA TCG
 R   F   Y   Y   R   G   K   R   L   L   S   Q   P   W   S   H   L   S 1251          1260          1269          1278          1287          1296
CAT CAA GCT ATT CTC CCC AAT AAA AGC TAT CGA AAT CCA GAG ATT TAT CCC ACT
 H   Q   A   I   L   P   N   K   S   Y   R   N   P   E   I   Y   P   T 1305          1314          1323          1332          1341          1350
GAT CAA AAC ATT AAA ATC ACT AGT TCT CTC GAT TGC GAT CAT GGA GCT TTT CTT
 D   Q   N   I   K   I   T   S   S   L   D   C   D   H   G   A   F   L 1359          1368          1377          1386          1395          1404
GGT GGA ACC TCG CTT ATT ATC AAA GGC CAA CGT TTC AAT CAT AGA GAA TCG CAT
 G   G   T   S   L   I   I   K   G   Q   R   F   N   H   R   E   S   H 1413          1422          1431          1440          1449          1458
GAT GTT GAA ACT GAA ATT AGT ATA CCT CTG TAT AAG CTT TCA TTA GAT GCT AGT
 D   V   E   T   E   I   S   I   P   L   Y   K   L   S   L   D   A   S
```

Amino acid sequence deduced from the novel Endo-β-N-acetylglucosaminidase gene, and the nucleotide sequence of the DNA encoding this amino acid sequence (Continued)

FIG. 7

```
        1467           1476           1485           1494           1503           1512
AAA GGA TGC TCA TTG CGT TAT ATT TAT AGA ACT TTG TTG ATG AAA GAT GTA AAG
 K   G   C   S   L   R   Y   I   Y   R   T   L   L   M   K   D   V   K 1521           1530           1539           1548           1557           1566
TTG ACA GTA GCA TGT CAC TTT TCG TTA AAA ACA AAC GAC TCA GTT AAT TTC TTC
 L   T   V   A   C   H   F   S   L   K   T   N   D   S   V   N   F   F 1575           1584           1593           1602           1611           1620
AAG GTA TGG CAG CCA GAT GAA AAT TTC TCT TTT GAA TAT GAT GAT GGA ATG AGA
 K   V   W   Q   P   D   E   N   F   S   F   E   Y   D   D   G   M   R 1629           1638           1647           1656           1665           1674
GCC ACT GTT ACA ACT GAA AAT TCT ACC GAA AGC AGA TGC TTT TTA TTA CGT ACA
 A   T   V   T   T   E   N   S   T   E   S   R   C   F   L   L   R   T 1683           1692           1701           1710           1719           1728
ACA GAA GAA GAT ACA GGA GAA AAT GAT TGG ATA ACA AAA ACT ATT AAT GTG CCT
 T   E   E   D   T   G   E   N   D   W   I   T   K   T   I   N   V   P 1737           1746           1755           1764           1773           1782
GCT GTT CCA GAA GGA AGT CAA TTA TAC ATT ACA AGA CTT GAA GTG AGC GTA GTA
 A   V   P   E   G   S   Q   L   Y   I   T   R   L   E   V   S   V   V 1791           1800           1809           1818           1827           1836
TTA GAT ACA GCT GGT TTA GTA GGT CTT GTT AAT CAA GTT ATT GCT TGC TTG GGA
 L   D   T   A   G   L   V   G   L   V   N   Q   V   I   A   C   L   G 1845           1854           1863           1872           1881           1890
TAT ATT AGC ATC ATA CCA ACT ATA AAT TCT GGA ATA AAA ACA GAT TCA TCA CGC
 Y   I   S   I   I   P   T   I   N   S   G   I   K   T   D   S   S   R 1899           1908           1917           1926           1935           1944
ATT ATT CAG GAT CTC TTT TGG AAA GAT CAG AAA TAT ACC AAA ATC GGA AAA GAA
 I   I   Q   D   L   F   W   K   D   Q   K   Y   T   K   I   G   K   E 1953           1962           1971           1980           1989           1998
AGT TTA GAC GAC ATA GCT CAA GAA GAA GTT CAT AGA TAT TAT GGA ACA TTG AAC
 S   L   D   D   I   A   Q   E   E   V   H   R   Y   Y   G   T   L   N 2007           2016           2025           2034           2043           2052
TGG GAA AAC ACA GCA AAT GTA GTA AAC GCT TGG GAG GAA ATA GAT TAC TAC AAC
 W   E   N   T   A   N   V   V   N   A   W   E   E   I   D   Y   Y   N 2061           2070           2079           2088           2097           2106
GTT TTT TAC AAA GAA AGT GAC GAC TCT GCA ACT CGC ATC TTT TTA GGA ACA GCA
 V   F   Y   K   E   S   D   D   S   A   T   R   I   F   L   G   T   A 2115           2124           2133           2142           2151           2160
TTC TGT AAT CAA TTT CGT GTA TCT GGT TTA GAT ATT ATT TTA TCT AAG CTA CCA
 F   C   N   Q   F   R   V   S   G   L   D   I   I   L   S   K   L   P 2169           2178           2187           2196           2205           2214
AAG ATA GTT ATT GAA GCT GTT AAC AAA GAA GGA TAC ATC TCT TCA AGT GGT AGC
 K   I   V   I   E   A   V   N   K   E   G   Y   I   S   S   S   G   S 2223           2232
ATA GAT TTG TCA TTA AAC TAG 3'
 I   D   L   S   L   N   *
```

Amino acid sequence deduced from the novel Endo-β-N-acetylglucosaminidase gene, and the nucleotide sequence of the DNA encoding this amino acid sequence (Continued)

Structure of expression vector pGEndo-SC for the use in *Saccharomyces cerevisiae*, which comprises a novel endo-β-N-acetylglucosaminidase gene

FIG. 9

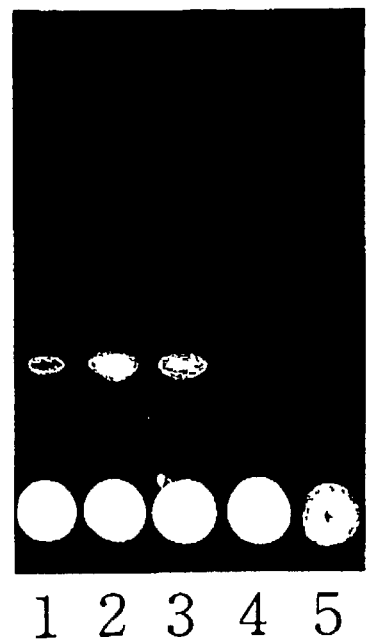

Expression of endo-β-N-acetylglucosaminidase enzyme in yeast into which an endo-β-N-acetylglucosaminidase gene has been introduced Lanes 1-3   Cellular extract of *S cerevisiae* YPH500 (pep4) into which an endo-β-N-acetylglucosaminidase gene has been introduced.

Lane 4   Purified endo-β-N-acetylglucosaminidase derived from *M. hiemalis*

Lane 5.   Cellular extract of *S. cerevisiae* YPH500 (pep4)

SEQUENCE LISTING

<160> NUMBER OF SEQ ID NOS: 37

<210> SEQ ID NO 1
<211> LENGTH: 2369
<212> TYPE: DNA
<213> ORGANISM: Mucor hiemalis

<400> SEQUENCE: 1

```
gtcgacccac gcgtccgcgg acgcgtgggc ggacgcgtgg gcggacgcgt gggttttatt      60
ttacataaat atgccttcac ttcaattgca acctgatgac aaactagcac ctgtttcttt     120
tgcacttaag tctatgaatg agttgaggga ctggacgcca gacgaaaaga taaagtttaa     180
cgtttcaagc gtggcactac agcctcgtgt gaaaaacgcc ctgaaacctc aattattgtt     240
aactcatgat atggcaggag gatataaaga agataaaaat attcaaggaa acaattataa     300
agacatttat aacattcaat attggcattt agctgatact tttgtatatt tctctcatga     360
gcgagttagc attcctccag tcaattggac aaatgcttgt catagaaatg gtgtaaagtg     420
tttaggtact ttttagtag aaggaaataa ccaaatgcat gaaatggaag ccttgcttca     480
cggtccacct ttacttaata acactgacga ccctatgaga ttatggagtc cgtattatgc     540
agaccaatta gttgctattg ctaaacacta tggttttgat ggctggttgt tcaatattga     600
atgcgaattc tttccttttc ctacaaatcc aaaattcaaa gctgaagagt tggcaaagtt     660
tctacactat tttaaggaaa aattgcataa cgaaatacct ggatctcaac tcatttggta     720
cgacagcatg acaatgaaag gagaaatcca ctggcagaac cagctcacat ggaaaaatga     780
gttattttt aaaaacacgg atggtatttt tttgaattat tggtggaaaa aagaataccc     840
tgaaatggcg cgtagagtag ctgaaggaat aggtagatca ggtttagaag tttattttgg     900
tacagatgta tggggaaggc atacttatgg tggcggtggt ttcaaatcat ataagggtgt     960
aaaaactgcc tactctgcaa tgacatcttc tgcattattt ggtatggcat ggacatacga    1020
gcatttcgaa aagtctgaat ttgaaaagat ggatcgtttg ttttggtgtg gtggtaaata    1080
ctctgactat cctcccccac ctcctaaaaa cccagatgac gaaaaagaag tagaaagcga    1140
tgatagtgaa gatgagctca tgtacggaca caagaaaggt attgctgaca cggtagaatc    1200
tattcctgta ccaggaacag attggttttgt taccaatttt gatagggggt ttggaaatag    1260
gttttattat agaggaaaga gattactttc tcagccttgg tcccatttat cgcatcaagc    1320
tattctcccc aataaaagct atcgaaatcc agagatttat cccactgatc aaaacattaa    1380
aatcactagt tctctcgatt gcgatcatgg agcttttctt ggtggaacct cgcttattat    1440
caaaggccaa cgtttcaatc atagagaatc gcatgatgtt gaaactgaaa ttagtatacc    1500
tctgtataag ctttcattag atgctagtaa aggatgctca ttgcgttata tttatagaac    1560
tttgttgatg aaagatgtaa agttgacagt agcatgtcac ttttcgttaa aaacaaacga    1620
ctcagttaat ttcttcaagg tatggcagcc agatgaaaat ttctcttttg aatatgatga    1680
tggaatgaga gccactgtta caactgaaaa ttctaccgaa agcagatgct ttttattacg    1740
tacaacagaa gaagatacag gagaaaatga ttggataaca aaaactatta atgtgcctgc    1800
tgttccagaa ggaagtcaat tatacattac aagacttgaa gtgagcgtag tattagatac    1860
agctggttta gtaggtcttg ttaatcaagt tattgcttgc ttgggatata ttagcatcat    1920
accaactata aattctggaa taaaaacaga ttcatcacgc attattcagg atctcttttg    1980
gaaagatcag aaatatacca aaatcggaaa agaaagtttta gacgacatag ctcaagaaga    2040
agttcataga tattatggaa cattgaactg ggaaaacaca gcaaatgtag taaacgcttg    2100
ggaggaaata gattactaca acgttttttta caaagaaagt gacgactctg caactcgcat    2160
ctttttagga acagcattct gtaatcaatt tcgtgtatct ggtttagata ttatttttatc    2220
taagctacca aagatagtta ttgaagctgt taacaaagaa ggatacatct cttcaagtgg    2280
tagcatagat ttgtcattaa actaggactt gaaataaaat attatgataa agaaaaaaaa    2340
```

```
aaaaaaaaaa aaaaaaaaag ggcggccgc                                    2369

<210> SEQ ID NO 2
<211> LENGTH: 2235
<212> TYPE: DNA
<213> ORGANISM: Mucor hiemalis
<220> FEATURE:
<221> NAME/KEY: CDS
<222> LOCATION: (1)..(2232)

<400> SEQUENCE: 2 atg cct tca ctt caa ttg caa cct gat gac aaa cta gca cct gtt tct      48
Met Pro Ser Leu Gln Leu Gln Pro Asp Asp Lys Leu Ala Pro Val Ser
 1               5                  10                  15 ttt gca ctt aag tct atg aat gag ttg agg gac tgg acg cca gac gaa      96
Phe Ala Leu Lys Ser Met Asn Glu Leu Arg Asp Trp Thr Pro Asp Glu
             20                  25                  30 aag ata aag ttt aac gtt tca agc gtg gca cta cag cct cgt gtg aaa     144
Lys Ile Lys Phe Asn Val Ser Ser Val Ala Leu Gln Pro Arg Val Lys
         35                  40                  45 aac gcc ctg aaa cct caa tta ttg tta act cat gat atg gca gga gga     192
Asn Ala Leu Lys Pro Gln Leu Leu Leu Thr His Asp Met Ala Gly Gly
     50                  55                  60 tat aaa gaa gat aaa aat att caa gga aac aat tat aaa gac att tat     240
Tyr Lys Glu Asp Lys Asn Ile Gln Gly Asn Asn Tyr Lys Asp Ile Tyr
 65                  70                  75                  80 aac att caa tat tgg cat tta gct gat act ttt gta tat ttc tct cat     288
Asn Ile Gln Tyr Trp His Leu Ala Asp Thr Phe Val Tyr Phe Ser His
                 85                  90                  95 gag cga gtt agc att cct cca gtc aat tgg aca aat gct tgt cat aga     336
Glu Arg Val Ser Ile Pro Pro Val Asn Trp Thr Asn Ala Cys His Arg
            100                 105                 110 aat ggt gta aag tgt tta ggt act ttt tta gta gaa gga aat aac caa     384
Asn Gly Val Lys Cys Leu Gly Thr Phe Leu Val Glu Gly Asn Asn Gln
        115                 120                 125 atg cat gaa atg gaa gcc ttg ctt cac ggt cca cct tta ctt aat aac     432
Met His Glu Met Glu Ala Leu Leu His Gly Pro Pro Leu Leu Asn Asn
    130                 135                 140 act gac gac cct atg aga tta tgg agt ccg tat tat gca gac caa tta     480
Thr Asp Asp Pro Met Arg Leu Trp Ser Pro Tyr Tyr Ala Asp Gln Leu
145                 150                 155                 160 gtt gct att gct aaa cac tat ggt ttt gat ggc tgg ttg ttc aat att     528
Val Ala Ile Ala Lys His Tyr Gly Phe Asp Gly Trp Leu Phe Asn Ile
                165                 170                 175 gaa tgc gaa ttc ttt cct ttt cct aca aat cca aaa ttc aaa gct gaa     576
Glu Cys Glu Phe Phe Pro Phe Pro Thr Asn Pro Lys Phe Lys Ala Glu
            180                 185                 190 gag ttg gca aag ttt cta cac tat ttt aag gaa aaa ttg cat aac gaa     624
Glu Leu Ala Lys Phe Leu His Tyr Phe Lys Glu Lys Leu His Asn Glu
        195                 200                 205 ata cct gga tct caa ctc att tgg tac gac agc atg aca aat gaa gga     672
Ile Pro Gly Ser Gln Leu Ile Trp Tyr Asp Ser Met Thr Asn Glu Gly
    210                 215                 220 gaa atc cac tgg cag aac cag ctc aca tgg aaa aat gag tta ttt ttt     720
Glu Ile His Trp Gln Asn Gln Leu Thr Trp Lys Asn Glu Leu Phe Phe
225                 230                 235                 240 aaa aac acg gat ggt att ttt ttg aat tat tgg tgg aaa aaa gaa tac     768
Lys Asn Thr Asp Gly Ile Phe Leu Asn Tyr Trp Trp Lys Lys Glu Tyr
                245                 250                 255 cct gaa atg gcg cgt aga gta gct gaa gga ata ggt aga tca ggt tta     816
```

-continued

```
        Pro Glu Met Ala Arg Arg Val Ala Glu Gly Ile Gly Arg Ser Gly Leu
                    260                 265                 270 gaa gtt tat ttt ggt aca gat gta tgg gga agg cat act tat ggt ggc          864
Glu Val Tyr Phe Gly Thr Asp Val Trp Gly Arg His Thr Tyr Gly Gly
            275                 280                 285 ggt ggt ttc aaa tca tat aag ggt gta aaa act gcc tac tct gca atg          912
Gly Gly Phe Lys Ser Tyr Lys Gly Val Lys Thr Ala Tyr Ser Ala Met
        290                 295                 300 aca tct tct gca tta ttt ggt atg gca tgg aca tac gag cat ttc gaa          960
Thr Ser Ser Ala Leu Phe Gly Met Ala Trp Thr Tyr Glu His Phe Glu
305                 310                 315                 320 aag tct gaa ttt gaa aag atg gat cgt ttg ttt tgg tgt ggt ggt aaa         1008
Lys Ser Glu Phe Glu Lys Met Asp Arg Leu Phe Trp Cys Gly Gly Lys
                325                 330                 335 tac tct gac tat cct ccc cca cct cct aaa aac cca gat gac gaa aaa         1056
Tyr Ser Asp Tyr Pro Pro Pro Pro Pro Lys Asn Pro Asp Asp Glu Lys
            340                 345                 350 gaa gta gaa agc gat gat agt gaa gat gag ctc atg tac gga cac aag         1104
Glu Val Glu Ser Asp Asp Ser Glu Asp Glu Leu Met Tyr Gly His Lys
        355                 360                 365 aaa ggt att gct gac acg gta gaa tct att cct gta cca gga aca gat         1152
Lys Gly Ile Ala Asp Thr Val Glu Ser Ile Pro Val Pro Gly Thr Asp
370                 375                 380 tgg ttt gtt acc aat ttt gat agg ggg ttt gga aat agg ttt tat tat         1200
Trp Phe Val Thr Asn Phe Asp Arg Gly Phe Gly Asn Arg Phe Tyr Tyr
385                 390                 395                 400 aga gga aag aga tta ctt tct cag cct tgg tcc cat tta tcg cat caa         1248
Arg Gly Lys Arg Leu Leu Ser Gln Pro Trp Ser His Leu Ser His Gln
                405                 410                 415 gct att ctc ccc aat aaa agc tat cga aat cca gag att tat ccc act         1296
Ala Ile Leu Pro Asn Lys Ser Tyr Arg Asn Pro Glu Ile Tyr Pro Thr
            420                 425                 430 gat caa aac att aaa atc act agt tct ctc gat tgc gat cat gga gct         1344
Asp Gln Asn Ile Lys Ile Thr Ser Ser Leu Asp Cys Asp His Gly Ala
        435                 440                 445 ttt ctt ggt gga acc tcg ctt att atc aaa ggc caa cgt ttc aat cat         1392
Phe Leu Gly Gly Thr Ser Leu Ile Ile Lys Gly Gln Arg Phe Asn His
450                 455                 460 aga gaa tcg cat gat gtt gaa act gaa att agt ata cct ctg tat aag         1440
Arg Glu Ser His Asp Val Glu Thr Glu Ile Ser Ile Pro Leu Tyr Lys
465                 470                 475                 480 ctt tca tta gat gct agt aaa gga tgc tca ttg cgt tat att tat aga         1488
Leu Ser Leu Asp Ala Ser Lys Gly Cys Ser Leu Arg Tyr Ile Tyr Arg
                485                 490                 495 act ttg ttg atg aaa gat gta aag ttg aca gta gca tgt cac ttt tcg         1536
Thr Leu Leu Met Lys Asp Val Lys Leu Thr Val Ala Cys His Phe Ser
            500                 505                 510 tta aaa aca aac gac tca gtt aat ttc ttc aag gta tgg cag cca gat         1584
Leu Lys Thr Asn Asp Ser Val Asn Phe Phe Lys Val Trp Gln Pro Asp
        515                 520                 525 gaa aat ttc tct ttt gaa tat gat gat gga atg aga gcc act gtt aca         1632
Glu Asn Phe Ser Phe Glu Tyr Asp Asp Gly Met Arg Ala Thr Val Thr
530                 535                 540 act gaa aat tct acc gaa agc aga tgc ttt tta tta cgt aca aca gaa         1680
Thr Glu Asn Ser Thr Glu Ser Arg Cys Phe Leu Leu Arg Thr Thr Glu
545                 550                 555                 560 gaa gat aca gga gaa aat gat tgg ata aca aaa act att aat gtg cct         1728
Glu Asp Thr Gly Glu Asn Asp Trp Ile Thr Lys Thr Ile Asn Val Pro
                565                 570                 575
```

```
gct gtt cca gaa gga agt caa tta tac att aca aga ctt gaa gtg agc    1776
Ala Val Pro Glu Gly Ser Gln Leu Tyr Ile Thr Arg Leu Glu Val Ser
            580                 585                 590 gta gta tta gat aca gct ggt tta gta ggt ctt gtt aat caa gtt att    1824
Val Val Leu Asp Thr Ala Gly Leu Val Gly Leu Val Asn Gln Val Ile
    595                 600                 605 gct tgc ttg gga tat att agc atc ata cca act ata aat tct gga ata    1872
Ala Cys Leu Gly Tyr Ile Ser Ile Ile Pro Thr Ile Asn Ser Gly Ile
610                 615                 620 aaa aca gat tca tca cgc att att cag gat ctc ttt tgg aaa gat cag    1920
Lys Thr Asp Ser Ser Arg Ile Ile Gln Asp Leu Phe Trp Lys Asp Gln
625                 630                 635                 640 aaa tat acc aaa atc gga aaa gaa agt tta gac gac ata gct caa gaa    1968
Lys Tyr Thr Lys Ile Gly Lys Glu Ser Leu Asp Asp Ile Ala Gln Glu
                645                 650                 655 gaa gtt cat aga tat tat gga aca ttg aac tgg gaa aac aca gca aat    2016
Glu Val His Arg Tyr Tyr Gly Thr Leu Asn Trp Glu Asn Thr Ala Asn
            660                 665                 670 gta gta aac gct tgg gag gaa ata gat tac tac aac gtt ttt tac aaa    2064
Val Val Asn Ala Trp Glu Glu Ile Asp Tyr Tyr Asn Val Phe Tyr Lys
        675                 680                 685 gaa agt gac gac tct gca act cgc atc ttt tta gga aca gca ttc tgt    2112
Glu Ser Asp Asp Ser Ala Thr Arg Ile Phe Leu Gly Thr Ala Phe Cys
    690                 695                 700 aat caa ttt cgt gta tct ggt tta gat att att tta tct aag cta cca    2160
Asn Gln Phe Arg Val Ser Gly Leu Asp Ile Ile Leu Ser Lys Leu Pro
705                 710                 715                 720 aag ata gtt att gaa gct gtt aac aaa gaa gga tac atc tct tca agt    2208
Lys Ile Val Ile Glu Ala Val Asn Lys Glu Gly Tyr Ile Ser Ser Ser
                725                 730                 735 ggt agc ata gat ttg tca tta aac tag                                2235
Gly Ser Ile Asp Leu Ser Leu Asn
            740
```

<210> SEQ ID NO 3
<211> LENGTH: 744
<212> TYPE: PRT
<213> ORGANISM: Mucor hiemalis

<400> SEQUENCE: 3

```
Met Pro Ser Leu Gln Leu Gln Pro Asp Asp Lys Leu Ala Pro Val Ser
 1               5                  10                  15

Phe Ala Leu Lys Ser Met Asn Glu Leu Arg Asp Trp Thr Pro Asp Glu
            20                  25                  30

Lys Ile Lys Phe Asn Val Ser Ser Val Ala Leu Gln Pro Arg Val Lys
        35                  40                  45

Asn Ala Leu Lys Pro Gln Leu Leu Leu Thr His Asp Met Ala Gly Gly
    50                  55                  60

Tyr Lys Glu Asp Lys Asn Ile Gln Gly Asn Asn Tyr Lys Asp Ile Tyr
65                  70                  75                  80

Asn Ile Gln Tyr Trp His Leu Ala Asp Thr Phe Val Tyr Phe Ser His
                85                  90                  95

Glu Arg Val Ser Ile Pro Pro Val Asn Trp Thr Asn Ala Cys His Arg
            100                 105                 110

Asn Gly Val Lys Cys Leu Gly Thr Phe Leu Val Glu Gly Asn Asn Gln
        115                 120                 125

Met His Glu Met Glu Ala Leu Leu His Gly Pro Pro Leu Leu Asn Asn
    130                 135                 140
```

-continued

```
Thr Asp Asp Pro Met Arg Leu Trp Ser Pro Tyr Tyr Ala Asp Gln Leu
145                 150                 155                 160

Val Ala Ile Ala Lys His Tyr Gly Phe Asp Gly Trp Leu Phe Asn Ile
                165                 170                 175

Glu Cys Glu Phe Pro Phe Pro Thr Asn Pro Lys Phe Lys Ala Glu
            180                 185                 190

Glu Leu Ala Lys Phe Leu His Tyr Phe Lys Glu Lys Leu His Asn Glu
            195                 200                 205

Ile Pro Gly Ser Gln Leu Ile Trp Tyr Asp Ser Met Thr Asn Glu Gly
        210                 215                 220

Glu Ile His Trp Gln Asn Gln Leu Thr Trp Lys Asn Glu Leu Phe Phe
225                 230                 235                 240

Lys Asn Thr Asp Gly Ile Phe Leu Asn Tyr Trp Trp Lys Lys Glu Tyr
                245                 250                 255

Pro Glu Met Ala Arg Arg Val Ala Glu Gly Ile Gly Arg Ser Gly Leu
            260                 265                 270

Glu Val Tyr Phe Gly Thr Asp Val Trp Gly Arg His Thr Tyr Gly Gly
        275                 280                 285

Gly Gly Phe Lys Ser Tyr Lys Gly Val Lys Thr Ala Tyr Ser Ala Met
    290                 295                 300

Thr Ser Ser Ala Leu Phe Gly Met Ala Trp Thr Tyr Glu His Phe Glu
305                 310                 315                 320

Lys Ser Glu Phe Glu Lys Met Asp Arg Leu Phe Trp Cys Gly Gly Lys
                325                 330                 335

Tyr Ser Asp Tyr Pro Pro Pro Pro Lys Asn Pro Asp Asp Glu Lys
            340                 345                 350

Glu Val Glu Ser Asp Asp Ser Glu Asp Glu Leu Met Tyr Gly His Lys
            355                 360                 365

Lys Gly Ile Ala Asp Thr Val Glu Ser Ile Pro Val Pro Gly Thr Asp
    370                 375                 380

Trp Phe Val Thr Asn Phe Asp Arg Gly Phe Gly Asn Arg Phe Tyr Tyr
385                 390                 395                 400

Arg Gly Lys Arg Leu Leu Ser Gln Pro Trp Ser His Leu Ser His Gln
                405                 410                 415

Ala Ile Leu Pro Asn Lys Ser Tyr Arg Asn Pro Glu Ile Tyr Pro Thr
            420                 425                 430

Asp Gln Asn Ile Lys Ile Thr Ser Ser Leu Asp Cys Asp His Gly Ala
            435                 440                 445

Phe Leu Gly Gly Thr Ser Leu Ile Ile Lys Gly Gln Arg Phe Asn His
    450                 455                 460

Arg Glu Ser His Asp Val Glu Thr Glu Ile Ser Ile Pro Leu Tyr Lys
465                 470                 475                 480

Leu Ser Leu Asp Ala Ser Lys Gly Cys Ser Leu Arg Tyr Ile Tyr Arg
                485                 490                 495

Thr Leu Leu Met Lys Asp Val Lys Leu Thr Val Ala Cys His Phe Ser
            500                 505                 510

Leu Lys Thr Asn Asp Ser Val Asn Phe Lys Val Trp Gln Pro Asp
            515                 520                 525

Glu Asn Phe Ser Phe Glu Tyr Asp Asp Gly Met Arg Ala Thr Val Thr
            530                 535                 540

Thr Glu Asn Ser Thr Glu Ser Arg Cys Phe Leu Leu Arg Thr Glu
545                 550                 555                 560

Glu Asp Thr Gly Glu Asn Asp Trp Ile Thr Lys Thr Ile Asn Val Pro
```

```
                      565                 570                 575
Ala Val Pro Glu Gly Ser Gln Leu Tyr Ile Thr Arg Leu Glu Val Ser
            580                 585                 590

Val Val Leu Asp Thr Ala Gly Leu Val Gly Leu Val Asn Gln Val Ile
            595                 600             605

Ala Cys Leu Gly Tyr Ile Ser Ile Ile Pro Thr Ile Asn Ser Gly Ile
            610             615                 620

Lys Thr Asp Ser Ser Arg Ile Ile Gln Asp Leu Phe Trp Lys Asp Gln
625                 630                 635                 640

Lys Tyr Thr Lys Ile Gly Lys Glu Ser Leu Asp Asp Ile Ala Gln Glu
                645                 650                 655

Glu Val His Arg Tyr Tyr Gly Thr Leu Asn Trp Glu Asn Thr Ala Asn
            660                 665                 670

Val Val Asn Ala Trp Glu Glu Ile Asp Tyr Tyr Asn Val Phe Tyr Lys
            675                 680             685

Glu Ser Asp Asp Ser Ala Thr Arg Ile Phe Leu Gly Thr Ala Phe Cys
    690                 695                 700

Asn Gln Phe Arg Val Ser Gly Leu Asp Ile Ile Leu Ser Lys Leu Pro
705                 710                 715                 720

Lys Ile Val Ile Glu Ala Val Asn Lys Glu Gly Tyr Ile Ser Ser Ser
                725                 730                 735

Gly Ser Ile Asp Leu Ser Leu Asn
            740

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Partial
      amino acid sequence of endo-beta-N-acetylglucosaminidase

<400> SEQUENCE: 4

Pro Ser Leu Gln Leu Gln Pro Asp Asp Lys
 1               5                  10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide based on the partial amino acid sequence of
      endo-beta-N-acetylglucosaminidase
<221> NAME/KEY: modified_base
<222> LOCATION: (12)
<223> OTHER INFORMATION: a, g, c or t

<400> SEQUENCE: 5
carttrcarc cngaygayaa                                              20

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Partial
      amino acid sequence of endo-beta-N-acetylglucosaminidase

<400> SEQUENCE: 6

Ser Tyr Arg Asn Pro Glu Ile Tyr Pro Thr Asp Gln Asn Ile Lys
 1               5                  10                  15
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide based on the partial amino acid sequence of
    endo-beta-N-acetylglucosaminidase
<221> NAME/KEY: modified_base
<222> LOCATION: (6)
<223> OTHER INFORMATION: a, g, c or t

<400> SEQUENCE: 7
cchacngayc araayatyaa                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide based on the partial amino acid sequence of
    endo-beta-N-acetylglucosaminidase
<221> NAME/KEY: modified_base
<222> LOCATION: (15)
<223> OTHER INFORMATION: a, g, c or t

<400> SEQUENCE: 8
ttratrttyt grtcngtdgg                                               20

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Partial
    amino acid sequence of endo-beta-N-acetylglucosaminidase

<400> SEQUENCE: 9

Gly Gln Arg Phe Asn His Arg Glu Ser His Asp Val Glu Thr Glu Ile
 1               5                  10                  15

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide based on the partial amino acid sequence of
    endo-beta-N-acetylglucosaminidase

<400> SEQUENCE: 10
tgrttraadc gytgdccytt                                               20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
    Oligonucleotide sequence of 5' terminal region of endo-beta-N-
    acetylglucosaminidase gene

<400> SEQUENCE: 11
atgccttcac ttcaattgca acc                                           23

<210> SEQ ID NO 12

```
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide sequence of 3' terminal region of endo-beta-N-
      acetylglucosaminidase gene

<400> SEQUENCE: 12
ctagtttaat gacaaatcta tgc                                           23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide designed based on the sequence of endo-beta-N-
      acetylglucosaminidase gene

<400> SEQUENCE: 13
cacttaagtc tatgaatgag                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide designed based on the sequence of endo-beta-N-
      acetylglucosaminidase gene

<400> SEQUENCE: 14
aatctctgga tttcgatagc                                               20

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide designed based on the sequence of endo-beta-N-
      acetylglucosaminidase gene

<400> SEQUENCE: 15
ggggcggccg cttttatttt acataaatat gccttcactt c                       41

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide designed based on the sequence of endo-beta-N-
      acetylglucosaminidase gene

<400> SEQUENCE: 16
cccgcggccg cctagtttaa tgacaaatct atgctacc                           38

<210> SEQ ID NO 17
<211> LENGTH: 10
<212> TYPE: PRT
<213> ORGANISM: Mucor hiemalis

<400> SEQUENCE: 17

Pro Ser Leu Gln Leu Gln Pro Asp Asp Lys
 1               5                  10
```

```
<210> SEQ ID NO 18
<211> LENGTH: 16
<212> TYPE: PRT
<213> ORGANISM: Mucor hiemalis

<400> SEQUENCE: 18

Lys Ser Tyr Arg Asn Pro Glu Ile Tyr Pro Thr Asp Gln Asn Ile Lys
 1               5                  10                  15

<210> SEQ ID NO 19
<211> LENGTH: 14
<212> TYPE: PRT
<213> ORGANISM: Mucor hiemalis

<400> SEQUENCE: 19

Lys Phe Asn Val Ser Ser Val Ala Leu Gln Pro Arg Val Lys
 1               5                  10

<210> SEQ ID NO 20
<211> LENGTH: 11
<212> TYPE: PRT
<213> ORGANISM: Mucor hiemalis
<220> FEATURE:
<221> NAME/KEY: MOD_RES
<222> LOCATION: (2)
<223> OTHER INFORMATION: Met or Ser

<400> SEQUENCE: 20

Lys Xaa Asp Arg Leu Phe Leu Cys Gly Gly Lys
 1               5                  10

<210> SEQ ID NO 21
<211> LENGTH: 17
<212> TYPE: PRT
<213> ORGANISM: Mucor hiemalis
<220> FEATURE:
<221> NAME/KEY: MOD_RES
<222> LOCATION: (2)
<223> OTHER INFORMATION: Gly or Met
<221> NAME/KEY: MOD_RES
<222> LOCATION: (3)
<223> OTHER INFORMATION: Gln or Ala
<221> NAME/KEY: MOD_RES
<222> LOCATION: (4)
<223> OTHER INFORMATION: Arg or Leu
<221> NAME/KEY: MOD_RES
<222> LOCATION: (6)
<223> OTHER INFORMATION: Asn or Pro
<221> NAME/KEY: MOD_RES
<222> LOCATION: (8)
<223> OTHER INFORMATION: Arg or Leu
<221> NAME/KEY: MOD_RES
<222> LOCATION: (9)
<223> OTHER INFORMATION: Glu or Leu
<221> NAME/KEY: MOD_RES
<222> LOCATION: (10)
<223> OTHER INFORMATION: Ser or Leu
<221> NAME/KEY: MOD_RES
<222> LOCATION: (11)
<223> OTHER INFORMATION: His or Thr

<400> SEQUENCE: 21

Lys Xaa Xaa Xaa Phe Xaa His Xaa Xaa Xaa Xaa Asp Val Glu Thr Glu
 1               5                  10                  15

Ile

<210> SEQ ID NO 22
<211> LENGTH: 16
<212> TYPE: PRT
```

```
<213> ORGANISM: Mucor hiemalis

<400> SEQUENCE: 22

Lys Glu Gly Tyr Ile Ser Ser Gly Ser Ile Asp Leu Ser Leu Asn
 1               5                  10                  15

<210> SEQ ID NO 23
<211> LENGTH: 9
<212> TYPE: PRT
<213> ORGANISM: Mucor hiemalis

<400> SEQUENCE: 23

Lys Asn Ile Gln Gly Asn Asn Tyr Lys
 1               5

<210> SEQ ID NO 24
<211> LENGTH: 11
<212> TYPE: PRT
<213> ORGANISM: Mucor hiemalis

<400> SEQUENCE: 24

Lys Tyr Ser Asp Tyr Pro Pro Pro Pro Lys
 1               5                  10

<210> SEQ ID NO 25
<211> LENGTH: 8
<212> TYPE: PRT
<213> ORGANISM: Mucor hiemalis

<400> SEQUENCE: 25

Lys Leu Ser Leu Asp Ala Ser Lys
 1               5

<210> SEQ ID NO 26
<211> LENGTH: 13
<212> TYPE: PRT
<213> ORGANISM: Mucor hiemalis

<400> SEQUENCE: 26

Lys Asn Thr Asp Gly Ile Phe Leu Asn Tyr Trp Trp Lys
 1               5                  10

<210> SEQ ID NO 27
<211> LENGTH: 15
<212> TYPE: PRT
<213> ORGANISM: Mucor hiemalis
<220> FEATURE:
<221> NAME/KEY: MOD_RES
<222> LOCATION: (3)
<223> OTHER INFORMATION: Carboxymethylcystein

<400> SEQUENCE: 27

Lys Gly Cys Ser Leu Arg Tyr Ile Tyr Arg Thr Leu Leu Met Lys
 1               5                  10                  15

<210> SEQ ID NO 28
<211> LENGTH: 7
<212> TYPE: PRT
<213> ORGANISM: Mucor hiemalis
<220> FEATURE:
<221> NAME/KEY: MOD_RES
<222> LOCATION: (6)
<223> OTHER INFORMATION: Carboxymethylcysteine

<400> SEQUENCE: 28

Lys Leu Thr Val Ala Cys His
```

-continued

```
<210> SEQ ID NO 29
<211> LENGTH: 15
<212> TYPE: PRT
<213> ORGANISM: Mucor hiemalis

<400> SEQUENCE: 29

Lys Pro Gln Leu Leu Leu Thr His Asp Met Ala Gly Gly Tyr Lys
 1               5                  10                  15

<210> SEQ ID NO 30
<211> LENGTH: 14
<212> TYPE: PRT
<213> ORGANISM: Mucor hiemalis

<400> SEQUENCE: 30

Lys Ser Met Asn Glu Leu Arg Asp Trp Thr Pro Asp Glu Lys
 1               5                  10

<210> SEQ ID NO 31
<211> LENGTH: 10
<212> TYPE: PRT
<213> ORGANISM: Mucor hiemalis

<400> SEQUENCE: 31

Lys Leu Ala Pro Val Ser Phe Ala Leu Lys
 1               5                  10

<210> SEQ ID NO 32
<211> LENGTH: 23
<212> TYPE: PRT
<213> ORGANISM: Mucor hiemalis

<400> SEQUENCE: 32

Lys Gly Gln Arg Phe Asn His Arg Glu Ser His Asp Val Glu Thr Glu
 1               5                  10                  15

Ile Ser Ile Pro Leu Tyr Lys
            20

<210> SEQ ID NO 33
<211> LENGTH: 22
<212> TYPE: PRT
<213> ORGANISM: Mucor hiemalis
<220> FEATURE:
<221> NAME/KEY: MOD_RES
<222> LOCATION: (8)
<223> OTHER INFORMATION: Carboxymethylcystein

<400> SEQUENCE: 33

Lys Ile Thr Ser Ser Leu Asp Cys Asp His Gly Ala Phe Leu Gly Gly
 1               5                  10                  15

Thr Ser Leu Ile Ile Lys
            20

<210> SEQ ID NO 34
<211> LENGTH: 19
<212> TYPE: PRT
<213> ORGANISM: Mucor hiemalis

<400> SEQUENCE: 34

Lys Asn Glu Leu Phe Phe Lys Asn Thr Asp Gly Ile Phe Leu Asn Tyr
 1               5                  10                  15

Trp Trp Lys
```

```
<210> SEQ ID NO 35
<211> LENGTH: 9
<212> TYPE: PRT
<213> ORGANISM: Mucor hiemalis

<400> SEQUENCE: 35

Lys Ile Val Ile Glu Ala Val Asn Lys
 1               5

<210> SEQ ID NO 36
<211> LENGTH: 11
<212> TYPE: PRT
<213> ORGANISM: Mucor hiemalis

<400> SEQUENCE: 36

Ser Ser Arg Ile Ile Gln Asp Leu Phe Trp Lys
 1               5                  10

<210> SEQ ID NO 37
<211> LENGTH: 14
<212> TYPE: PRT
<213> ORGANISM: Mucor hiemalis

<400> SEQUENCE: 37

Lys Thr Asp Ser Ser Arg Ile Ile Gln Asp Leu Phe Trp Lys
 1               5                  10
```

ENDO-β-N-ACETYLGLUCOSAMINIDASE GENE

TECHNICAL FIELD

The present invention relates to a novel endo-β-N-acetylglucosaminidase gene, and specifically relates to a gene where said gene is derived from the genus *Mucor*. Further, the present invention relates to a recombinant plasmid which comprises said gene, an organism transformed with said plasmid, and a method of producing a novel endo-β-N-acetylglucosaminidase using said transformant.

BACKGROUND ART

Glycoproteins are widely found in animal tissue, plant tissue, and the cell membrane and cell wall etc. of eukaryotic microorganisms.

In recent years, it has become increasingly clear that the sugar chains of glycoproteins play an important role in mechanisms such as cell differentiation, carcinogenesis and intercellular recognition. In order to clarify these mechanisms, research into the correlation between sugar chain structure and its function is proceeding. As a means of achieving this objective, when cleaving a sugar chain from a glycoprotein or when identifying the structure of a sugar chain, various glycosidases are employed. Among these, endo-β-N-acetylglucosaminidase acts on the asparagine-linked sugar chain (N-linked sugar chain, N-sugar chain) and has the action of cleaving the diacetyl-chitobiose portion that exists within the sugar chain thereby liberating the sugar chain.

Since endo-β-N-acetylglucosaminidase can liberate the sugar portion of a glycoprotein from the protein portion, it is thought to be important in the analysis of the function and structure of sugar chains in glycoproteins.

Asparagine-linked sugar chains may be classified by their structure as high mannose type (mannane type sugar chain), hybrid type, or complex type.

Known endo-β-N-acetylglucosaminidases include Endo H (A. L. Tarentino and F. Maley, *J. Biol. Chem.*, 249, 811 (1974)), Endo F (K. Takegawa, et al., *Eur. j. Biochem.*, 202, 175 (1991)), and EndoA (K. Takegawa, et al., *Appl. Environ. Microbiol.*, 55, 3107 (1989)). However, these enzymes only act upon sugars with specific structures, and do not act upon glycoproteins except in the presence of a denaturing agent.

Endo-β-N-acetylglucosaminidase derived from *Mucor hiemalis* is capable of cleaving tri-antennary complex type sugar chains in respect of not only high mannose type (mannane type sugar chain) and hybrid type, but also complex type chains. Further, with the asialylated type, cleavage ability extends to tetra-antennary heteroglycan chains. Further, it is known that it is possible to free sugar chains from glycoproteins without subjecting the protein to denaturization treatment. (S. Kadowaki, et al., *Agric. Biol. Chem.*, 54, 97 (1990)). Therefore, endo-β-N-acetylglucosaminidase derived from *Mucor hiemalis* can be said to be useful in the research of the functional and physiological role of sugar chains and proteins of glycoproteins.

On the other hand, conversion of mannane type sugar chains derived from yeast into sugar chains in a form compatible with humans, is extremely significant industrially. As methods for this conversion, in vivo conversion through improvement of the yeast sugar chain biosynthetic system by genetic manipulation, and in vitro conversion using the trans-glycosylation reaction can be considered. For the purpose of sugar conversion, endo-β-N-acetylglucosaminidase is required to have as properties, 1) the substrate specificity, i.e an ability to cleave both mannane and complex types; and, 2) the ability to perform the trans-glycosylation reaction, which is the reverse reaction of the decomposition reaction. Therefore, endo-β-N-acetylglucosaminidase derived from *Mucor hiemalis* can be said to be an appropriate enzyme for the practice of said conversion.

The present inventors, have proposed a sugar chain conversion technique using endo-β-N-acetylglucosaminidase derived from *Mucor hiemalis* which can alter yeast sugar chains to human-compatible form. (Japanese Patent Application Laid-Open No: Hei 7-59587)

To perform sugar chain conversions such as the above, an authentic enzyme preparation of high purity is required in great amounts. In this case, improvement of enzyme productivity by conventional breeding methods using mold cells has been considered. However, since conventional breeding methods are limited predominantly to the method of selecting such an enzyme from mutant strains obtained using ultraviolet light or mutagens, the isolation of stable mutants is difficult. Further, conventional breeding methods are often accompanied by unfavorable transformations. Further, since molds generally produce protease enzymes, they are unfavorable for production of an enzyme for the purpose of sugar conversion. Since, in order to overcome these problems it is necessary to proceed through a number of purification steps, the work is complicated and the yield is low. For example, culturing a microorganism belonging to the genus *Mucor* which is a type of filamentous mold, even if purification of the supernatant of this culture is performed, contamination with protease cannot be prevented and preparation in large amounts is difficult because of low enzyme productivity of the microorganism, and thus this method was of little practical value.

Given the above, it is desired for the purpose of mass producing endo-β-N-acetylglucosaminidase, that the gene for said enzyme be obtained and produced through the use of genetic engineering. Further, if the gene can be obtained, it can be expected that an enzyme with improved heat resistance and pH resistance and increased reaction rate can be obtained using protein engineering techniques. However, there have been no reported attempts at gene cloning to date.

DISCLOSURE OF INVENTION

It is an object of the present invention to provide an endo-β-N-acetylglucosaminidase, an endo-β-N-acetylglucosaminidase gene, a recombinant vector which comprises said gene, an organism transformed with said vector, and a method of producing endo-β-N-acetylglucosaminidase.

The present inventors, as a result of their intensive research directed to solving the above problem, based on partial amino acid sequence information of said endo-β-N-acetylglucosaminidase derived from *Mucor hiemalis*, have succeeded in obtaining the gene that encodes said enzyme from a cDNA library prepared from *Mucor hiemalis* which is a bacteria which produces said enzyme, have further succeeded in expressing this gene in yeast, and thereby completed the present invention.

Thus, the present invention provides the recombinant protein of (a) or (b) below:

(a) a protein comprising the amino acid sequence represented by SEQ ID NO: 3; and, (b) a protein comprising an amino acid sequence derived from the amino acid sequence represented by SEQ ID NO: 3 by deletion, substitution, insertion, or addition of at least one amino acid and having the activity of endo-β-N-acetylglucosaminidase.

Further, the present invention provides a endo-β-N-acetylglucosaminidase gene which encodes the protein of (a) or (b) below, and a gene that hybridizes with said gene under stringent conditions, and which comprises DNA encoding a protein that has endo-β-N-acetylglucosaminidase activity.

(a) a protein comprising the amino acid sequence represented by SEQ ID NO: 3; and, (b) a protein comprising an amino acid sequence derived from the amino acid sequence represented by SEQ ID NO: 3 by deletion, substitution, insertion, or addition of at least one amino acid and having the activity of endo-β-N-acetylglucosaminidase.

Further, the present invention provides a gene comprising the DNA of (c) or (d) below:

(c) a DNA consisting of the nucleotide sequence represented by SEQ ID NO: 2; and, (d) a DNA which hybridizes under stringent conditions with a DNA consisting of the nucleotide sequence represented by SEQ ID NO: 2, and encodes a protein having the activity of endo-β-N-acetylglucosaminidase.

Said gene includes a gene derived from a microorganism belonging to the genus *Mucor*.

Further, the present invention provides a recombinant vector which comprises said gene.

Further, the present invention provides a transformant which comprises said recombinant vector.

Further, the present invention provides a method for producing an endo-β-N-acetylglucosaminidase, comprising culturing said transformant, and collecting endo-β-N-acetylglucosaminidase from the obtained culture product.

Below, the present invention will be described in detail.

The present invention is characterized by culturing endo-β-N-acetylglucosaminidase producing microorganisms, purifying the endo-β-N-acetylglucosaminidase from the obtained culture, designing degenerate probes from a partial amino acid sequence of said enzyme, cloning a gene encoding said enzyme by performing PCR, and further, cloning a gene encoding said enzyme from a cDNA library of the microorganism producing endo-β-N-acetylglucosaminidase. Further, the present invention is characterized by obtaining a recombinant vector by introducing the cloned gene into a vector, as well as by obtaining a transformant by introducing said recombinant vector into a host cell. Further, the present invention is characterized by producing endo-β-N-acetylglucosaminidase in large quantities by culturing said transformant.

1. Culturing of Endo-β-N-acetylglucosaminidase Producing Microorganisms

Microorganisms for producing endo-β-N-acetylglucosaminidase include microorganisms belonging to the genus *Mucor*, preferably *Mucor hiemalis*, and more preferably the *Mucor hiemalis* deposited at the National Institute of Bioscience and Human-Technology, Agency of Industrial Science and Technology (1-1-3, Higashi, Tsukuba-shi, Ibaraki-ken, Japan) (Accession No. FERM BP-4991).

The medium composition used in culturing of these strains may be of any kind typically used in the culture of microorganisms.

Carbon sources include for example sugars such as glucose, sucrose, mannose, galactose, maltose, soluble starch and dextrin. Nitrogen sources include yeast extract, trypton, etc. As inorganic salts, apart from the inorganic salts contained in the above nitrogen sources, salts such as all varieties of sodium salts, potassium salts, calcium salts, magnesium salts and phosphate salts may be used. Vitamins may be added optionally.

The culture medium is sterilized by a conventional method, and the strain is inoculated into the medium. Thereafter, a shake culture, or aeration-agitation culture is performed at 20–30° C., pH 5–7 for 2 to 4 days.

In the present invention, culture is preferably performed at 25–30° C., pH 6, with galactose as the carbon source, yeast extract and trypton as the nitrogen sources, with concentrations of both carbon and nitrogen sources at 2–3% each, and the ratio of carbon source to nitrogen source at 2:3, for 3 to 4 days under good aeration conditions. Where the culture is performed under such conditions, the amount of enzyme produced is maximized, and in comparison to the known method (S. Kadowaki, et al., *Agric. Biol. Chem.*, 54, 97 (1990); glucose 0.5%, yeast extract 1%, peptone 1%), about 10-fold greater productivity can be achieved.

Further, in the present invention, to ensure the aeration conditions when culturing the microorganisms, use of a jar fermenter is preferable.

2. Purification of Endo-β-N-acetylglucosaminidase

The endo-β-N-acetylglucosaminidase produced by the above bacterial strain is characterized by preservation of the following activity. In other words, it can be characterized by its activity to act on the asparagine-linked sugar chain in a glycoprotein, cleave the diacetyl-chitobiose portion within the sugar chain, and thereby liberate the sugar chain.

Purification of endo-β-N-acetylglucosaminidase can be performed by the appropriate combination of known methods for separation and purification. Examples of such methods include methods using differences in solubility such as salt precipitation and solvent precipitation; methods using differences in molecular weight such as dialysis, ultrafiltration, gel filtration and SDS-polyacrylamide electrophoresis; methods using differences in electrostatic charge such as ion exchange chromatography; methods using differences in hydrophobicity such as hydrophobic chromatography and reverse phase chromatography, and methods using differences in isoelectric point such as isoelectric focusing.

In the present invention, by adopting a method of culturing which is an improvement over the above described known method (S. Kadowaki, et al., *Agric Biol. Chem.*, 54, 97 (1990)), and subjecting to many purification steps, endo-β-N-acetylglucosaminidase can be efficiently purified, and it is possible to obtain a sufficient amount of the protein to determine the amino acid sequence necessary to obtain the gene. The obtained enzyme, as a result of purification and as a result of the analysis of the gene to be described below, consists of a single gene product with a molecular weight of approximately 85,000, and after post-translational partial digestion of the gene product, it was found to be composed of 2 or more subunits including peptides with molecular weights of approximately 60,000 and 14,000.

3. Cloning of the Novel Endo-β-N-acetylglucosaminidase Gene

It was clear that the endo-β-N-acetylglucosaminidase obtained from *Mucor hiemalis* was composed of at least 2 or more peptides.

Generally, when isolating a gene encoding a specific protein, a partial amino acid sequence of the protein is determined, and it is possible to isolate the desired gene from a gene library with a mixture of oligonucleotides consisting of degenerative codons as a probe. Further, after obtaining a fragment by PCR such as in the present invention, it is possible to isolate the desired gene from a gene library using this fragment as a probe.

However, since endo-β-N-acetylglucosaminidase is a hetero-oligomeric molecule consisting of 2 or more subunits, there is the possibility that each subunit is encoded independently by their separate differing genes. Further, even if endo-β-N-acetylglucosaminidase is derived from one gene, its structure, for example, the positional relationship between the regions encoding the two subunits within the structural gene was unclear.

Thus, the present inventors determined partial amino acid sequences for 2 subunits, and then after obtaining partial fragments by PCR, used said fragments as probes to achieve cDNA cloning and by analyzing the gene structure, clarified that the same gene coded for these 2 subunits. That is, it was clarified that the novel endo-β-N-acetylglucosaminidase is produced as one polypeptide from the gene encoding this enzyme, and is processed by partial decomposition into 2 or more subunits.

The gene of the present invention is cloned by, for example, the following method.

(1) Cloning of the Endo-β-N-acetylglucosaminidase Gene

In the present invention, an example of a DNA fragment comprising a gene encoding a novel endo-β-N-acetylglucosaminidase is the DNA fragment indicated by the restriction enzyme map shown in FIG. 2. This fragment can be isolated using genetic engineering methods from a cDNA library with an mRNA template prepared from a microorganism belonging to the genus *Mucor*, preferably from a strain of *Mucor hiemalis*, and more preferably from the strain of *Mucor hiemalis* deposited under accession number FERM BP-4991 at the National Institute of Bioscience and Human-Technology, (See the method described in, for example, *Molecular Cloning: A Laboratory Manual* (Sambrook, Maniatis et al, Cold Spring Harbour Laboratory Press (1989))

Preparation of mRNA can be performed according to a typical method. For example, after culturing the mRNA source, *Mucor hiemalis*, total RNA is obtained from the cultured cell with a kit available on the market (ISOGEN (Nippon Gene Company)), and then purified with a purification kit available on the market (mRNA Purification Kit (Pharmacia Biotech)). In the preparation of mRNA, it is preferable to keep the culturing time short to control the decomposition of mRNA.

With the thus obtained mRNA as a template, a single-strand cDNA is synthesized using an oligo dT primer and a reverse transcriptase enzyme. Thereupon, a duplex cDNA is synthesized from said single stranded cDNA. A recombinant vector is then constructed by incorporating the duplex cDNA into a suitable cloning vector. A cDNA library can be obtained by transforming *E.coli* using the obtained recombinant vector, and selecting or transformants using tetracycline resistance and ampicillin resistance as an indicator.

Here, transformation of *E.coli* is performed according to a method such as the Hanahan method [Hanahan, D.: *J. Mol. Biol.* 166: 557–580 (1983)]. When a plasmid is to be used as a vector, it is necessary to include a gene for resistance to a drug such as tetracycline or ampicillin. Further, a cloning vector other than a plasmid, for example, λ phage or the like can be used.

A strain having the desired DNA is selected (screened) from the thus obtained transformant. Screening methods include, for example, a method of synthesizing sense and antisense primers corresponding to a partial amino acid sequence of endo-β-N-acetylglucosaminidase, and using this to perform a polymerase chain reaction (PCR). Template DNA may include for example, genomic DNA or cDNA synthesized by reverse transcription from the above-mentioned mRNA. As primers, in respect of the sense chain, for example, 5'-CARTTRCARCCNGAYGAYAA-3' (SEQ ID NO: 5) synthesized on the basis of amino acid sequence: PSLQLQPDDK (SEQ ID NO: 4) and 5'-CCHACNGAYCARAAYATYAA-3' (SEQ ID NO: 7) synthesized on the basis of amino acid sequence: SYRN-PEIYPTDQNIK (SEQ ID NO: 6), may be used. Further, in respect of the antisense chain 3'-GGDTGNCTRGTYTTRTARTT-5' (SEQ ID NO: 8) synthesized on the basis of amino acid sequence: SYRN-PEIYPTDQNIK (SEQ ID NO: 6) and 3'-TTYCCDGTYGCDAARTTRGT-5' (SEQ ID NO: 10) synthesized on the basis of amino acid sequence: GQRFN-HRESHDVETEI (SEQ ID NO: 9), may be used. However, the present invention is not limited to these primers.

Thus, the obtained DNA amplification fragment is labeled with for example $^{32}P$, $^{35}S$ or biotin and taken as a probe, and is then made to hybridize with the cDNA library of the transformant, which library has been denatured and immobilized onto a nitrocellulose filter. Screening can then be performed by searching the obtained positive strains.

(2) Determination of the Nucleotide Sequence

Determination of the nucleotide sequence of the obtained clone is performed. Determination of the nucleotide sequence may be performed by known methods such as the Maxam-Gilbert chemical modification method or dideoxy method, though typically determination of the sequence is performed using an automated nucleotide sequencer. (For example, PERKIN-ELMER 377A DNA Sequencer)

The full length sequence of the endo-β-N-acetylglucosaminidase gene is indicated by SEQ ID NO: 1. Therein, a preferable example of the gene of the present invention, is the nucleotide sequence from position 71 to position 2305 (SEQ ID NO: 2) of the nucleotide sequence indicated by SEQ ID NO: 1. Further, the gene of the present invention includes not only a sequence which encodes the amino acid sequence represented by SEQ ID NO: 3 or the below described amino acid sequence having an equivalent sequence, but also encompasses degenerate isomers encoding identical polypeptides which differ in respect of degenerate codons only.

A nucleotide sequence encoding an amino acid sequence having an equivalent sequence can be prepared using a method such as site-directed mutagenesis. That is, mutations may be introduced by known methods such as the Kunkel method or Gapped duplex method, or other methods equivalent thereto, using for example a mutation introduction kit that employs site-directed mutagenesis (e.g. Mutant-K (Takara), Mutant-G (Takara)) etc., or using Takara's LA PCR in vitro Mutagenesis series kit.

Further, an endo-β-N-acetylglucosaminidase gene includes not only DNA consisting of the nucleotide sequence represented by SEQ ID NO: 1 or SEQ ID NO: 2, but also a DNA which hybridizes under stringent conditions with said DNA, and encodes a protein having the activity of endo-β-N-acetylglucosaminidase. Stringent conditions refer to, for example, the conditions of a sodium concentration of 50–300 mM, preferably 105 mM and a temperature of (50–68° C., preferably 65° C.

Once the nucleotide sequence of the endo-β-N-acetylglucosaminidase gene (SEQ ID NO: 1) is identified, since the nucleotide sequence of the DNA fragment having the sequence from position 71 to 2305 of the said nucleotide sequence (open reading frame) is determined (SEQ ID NO: 2), it is possible to obtain the endo-w-N-acetylglucosaminidase gene by chemical synthesis; by PCR with genomic DNA as a template and the 5' and 3' terminal sequences of the open reading frame (SEQ ID NO: 2) (e.g. 5'-ATGCCTTCACTTCAATTGCAACC-3' (SEQ ID NO: 11) and 5'-CTAGTTTAATGACAAATCTATGC-3' (SEQ ID NO: 12) as primers; or, by hybridization with a DNA fragment having the nucleotide sequence of an endo-β-N-acetylglucosaminidase gene as a probe.

The plasmid pZL-Endo (See Example 3 below) which comprises the gene of the present invention was introduced into *E.coli* DH10B (Title: DHBpZL-Endo) and deposited at National Institute of Bioscience and Human-Technology (1-1-3, Higashi, Tsukuba-shi, Tbaraki-ken, Japan) on Apr. 28, 1998 under accession number FERM BP-6335.

In the present invention, the amino acid sequence represented by SEQ ID NO: 3 or a polypeptide comprising an equivalent sequence, is provided as a preferable example of a recombinant novel endo-β-N-acetylglucosaminidase. Here, "equivalent sequence" refers to a sequence which comprises the amino acid sequence represented by SEQ ID NO: 3 and in which at least one amino acid is inserted, substituted, deleted or added to either end, and which retains said novel endo-β-N-acetylglucosaminidase activity. Retention of novel endo-β-N-acetylglucosaminidase activity in this equivalent sequence means that the sequence maintains activity sufficient for it to be used in an almost identical manner under identical conditions to the polypeptide having the full sequence represented by SEQ ID NO: 3 in actual forms of use which exploit this activity. It is clear that it is possible for a person skilled in the art to select and produce with no particular difficulty such an equivalent sequence; referring to the sequence represented by SEQ ID NO: 3. For example, within the amino acid sequence represented by SEQ ID NO: 3, at least 1, preferably 1 to 10, more preferably 1 to 5 amino acids may be deleted; at least 1, preferably 1 to 10, more preferably 1 to 5 amino acids may be added or inserted; or, at least 1, preferably 1 to 10, more preferably 1 to 5 amino acids may be substituted. Accordingly, the protein of the present invention includes a polypeptide having the amino acid sequence from position 2 to 744 of the amino acid sequence represented by SEQ ID NO: 3 in the Sequence Listing (one in which the methoinine at position 1 of the amino acid sequence represented by SEQ ID NO: 3 has been deleted.) Here, through the partial amino acid sequence analysis of the present invention and gene structure analysis, it became clear that 2 or more natural type subunits were produced by cleavage of a precursor polypeptide on the C terminal side of at least the histidine at position 510 and the asparagine at position 627 in the amino acid sequence represented by SEQ ID NO: 3.

2. Construction of a Recombinant Vector and Transformant

The present invention provides a DNA molecule comprising the gene of the present invention, in particular, an expression vector. This DNA molecule can be obtained by incorporating a DNA fragment encoding the novel endo-β-N-acetylglucosaminidase according to the present invention into a vector molecule. Accordingly, if transformation of a host cell is performed with a DNA molecule, particularly in the form of an expression vector, which includes a DNA fragment encoding the novel endo-β-N-acetylglucosaminidase of the present invention in a form such that it is replicable within the host cell and the said gene is expressible, it is possible to cause production of the novel endo-β-N-acetylglucosaminidase of the present invention in the host cell.

The DNA molecule according to this invention can be constructed based on the method described in the above-referenced *Molecular Cloning: A Laboratory Manual* (supra).

(1) Construction of a Recombinant Vector

The vector to be used in the present invention may be appropriately selected from a virus, plasmid, cosmid vector or the like in consideration of the type of host cell to be used.

For example, where the host cell is *E.coli*, bacteriophages of the λ phage line, plasmids of the pBR line (pBR322, pBR325 etc.) and pUC line (pUC118, pUC119 etc); where the host cell is *Bacillus subtilis*, plasmids of the pUB line (pUB110 etc); and where the host cell is yeast, vectors of the YEp and YCp lines (e.g. YEp13, YEp24, YCp50 etc.), or pG-3-Not used in the Examples below, may be used. Further, animal viruses such as a retrovirus or vaccinia virus, or insect virus vectors such baculovirus can be used.

To introduce the gene of the present invention into the vector, methods for ligating the gene to the vector such as first cleaving the purified DNA with a suitable restriction enzyme, and then inserting the gene at suitable restriction sites or multicloning sites of the vector DNA, are employed.

It is necessary that the gene of the present invention be incorporated into the vector such that the function of this gene is exhibited. Thus, it is preferable that the vector of the present invention includes a selective marker. Drug-resistant markers and auxotrophic markers can be used as selective markers.

Further, it is preferable that the DNA molecule to be used as the expression vector of the present invention has DNA sequences necessary for the expression of the novel endo-β-N-acetylglucosaminidase gene such as transcription regulating signals and translation regulating signals such as, for example, a promoter, transcription initiation signal, ribosome binding site, translation stop signal and a transcription termination signal.

(2) Construction of the Transformant

The transformant of the present invention can be obtained by introducing the recombinant vector of the present invention into a host in a manner allowing expression of the subject gene. There is no particular limitation on the host that may be used as long as it allows expression of the gene of the present invention. Examples include bacteria of the genus *Escherichia* such as *Escherichia coli*, of the genus *Bacillus* such as *Bacillus subtilis*, or of the genus *Pseudomonas* such as *Pseodomonas putida* etc., and yeasts such as *Saccharomyces cerevisiae, Schizosaccharomyces pombe, Candida boidinii* and *Pichia pastoris*.

As host cells, apart from *E.coli, B. subtilis,* and yeast, animal cells such as COS cells and CHO cells etc., and insect cells such as Sf9 and Sf21 etc. may be used.

Where a bacterium such as *E.coli* is used as a host, the recombinant vector of the present invention preferably is autonomously replicable within the bacterium and comprises a promoter, ribosome binding site, the gene of the present invention, and a transcriptional termination sequence. A gene which controls the promoter may also be included.

Examples of *E. coli* include *Escherichia coli* K12, DH1, DH5α, JM109 etc. Examples of *Bacillus subtilis* include *Bacillus subtilis* MI 114, 207–21 etc. It is known that there exist strains of *Bacillus subtilis* that secrete proteins out of the microorganism body. There are also known strains that secrete hardly any protease. The use of such strains as hosts is preferable.

As a promoter, a promoter within the inserted fragment that is able to function even in the host, may of course be used. Examples of promoters in *E.coli* include lactose operon (Oac) and tryptophan operon (trp), etc.

As a method for introducing the recombinant vector into bacteria, any method for introducing DNA into bacteria may be employed and there is no particular limitation thereon. Examples include a method using calcium ions [Cohen, S.N. et al.: *Proc. Natl. Acad. Sci., USA*, 69:2110–2114(1972)], and electroporation.

Where yeast is to be the host, *Saccharomyces cerevisiae, Schizosaccharomyces pombe, Candida utilis*, etc., may be used. In this case, there is no particular limitation on the promoter that may be used as long as it can express in yeast. For example, promoters such as alcohol dehydrogenase (ADH), acidic phosphatase (PHO), galactose gene (GAL), and glyceraldehyde-3-phosphate dehydrogenase gene (GAPDH) promoters, heat shock protein promoter, MFα1 promoter, PGK promoter, GAP promoter and AOX1 promoter may preferably be used.

As a method for introducing the recombinant vector into yeast, any method for introducing DNA into yeast may be employed and there is no particular limitation thereon. Examples include electroporation [Becker, D. M. et al.: *Methods. Enzymol.*, 194: 182–187 (1990)], spheroplast method [Hinnen, A. et al.: *Proc. Natl. Acad. Sci., USA*, 75: 1929–1933 (1978)], and lithium acetate method [Itoh, H.: *J. Bacteriol.*, 153:163–168 (1983)].

Where an animal cell is to be the host, monkey cell COS-7, Vero, Chinese hamster ovary cell (CHO cell), mouse L cell, rat GH3 and human FL cell, etc. may be used. As a promoter, SR α promoter, SV40 promoter, LTR promoter, CMV promoter or the like can be used. Also, the initial promoter of human cytomegalovirus or the like may be used.

Examples of a method for introducing the recombinant vector into an animal cell include electroporation, calcium phosphate method and lipofection method.

Where an insect cell is to be the host, Sf9 cell, Sf21 cell and the like may be used.

Examples of a method for introducing the recombinant vector into an insect cell include calcium phosphate method, lipofection, and electroporation.

4. Production of the Protein of the Present Invention

A protein of the present invention has an amino acid sequence encoded by a gene of the present invention, or has said amino acid sequence into which said modification of at least 1 amino acid has been introduced, and has the activity of endo-β-N-acetylglucosaminidase.

The protein of the present invention can be obtained by culturing the above-mentioned transformant and collecting the protein from this culture product. "Culture product" refers to either the culture supernatant, the cultured cells or microbial cells, or disrupted cells or microbial cells.

Either a natural medium or synthetic medium may be used as a medium for culturing transformants obtained with microorganisms such as *E. coli* or yeast as hosts, as long as it contains a carbon source, a nitrogen source, inorganic salts and the like, which are able to be assimilated by the microorganism and it may be used to efficiently perform a culture of the transformant.

As carbon sources, carbohydrates such as glucose, fructose, sucrose and starch, organic acids such as acetic acid and propionic acid, and alcohols such as ethanol and propanol are used.

As nitrogen sources, inorganic acids such as ammonia, ammonium chloride, ammonium sulfate, ammonium phosphate, organic acids such as ammonium acetate, or other nitrogen containing compounds, as well as peptone, meat extract, corn steep liquor or the like are used.

As inorganic matter, potassium (I) phosphate, potassium (II) phosphate, magnesium phosphate, magnesium sulfate, sodium chloride, iron (I) sulfate, manganese sulfate, copper sulfate and calcium carbonate, etc are used.

Culturing is typically performed under aerobic conditions such as a shake culture or aeration-agitation culture, at 37° C. at 12 to 72 hours. During culturing, pH is maintained at 4–7.5. Regulation of pH is performed using inorganic or organic acid or alkali solutions and the like.

During culturing, antibiotics such as ampicillin and tetracycline may be added to the medium as required.

When the microorganism transformed with an expression vector containing an inducible promoter is cultured, an inducer may he added to) the culture as required. For example, when culturing a microorganism transformed with an expression vector which uses a Lac promoter, isopropyl-β-D-thiogalactoside (EPIG) and the like may be added to the culture, and when culturing a microorganism transformed with an expression vector using a trp promoter, indole acetic acid (IAA) may be added.

As culture media for culturing a transformant obtained from an animal host cell, the generally used RPMI1640 medium, DMEM medium or these medium to which fetal calf serum and the like have been added, are used.

Culturing is typically performed over 2 to 10 days at 37° C. in the presence of 5% $CO_2$. Antibiotics such as kanamycin and penicillin and the like may be added during culturing as required.

After culturing, when the protein of the present invention has been produced within the microorganisms or cells, the protein of the present invention is extracted by disrupting the microorganisms or cells. When the protein of the present invention has been produced outside the microorganisms or cells, the culture fluid may be used as is, or the microorganisms or cells removed by centrifugal isolation, etc.

Purification of the recombinant novel endo-β-N-acetylglucosaminidase, is performed by the suitable combination of known separation and purification methods. Examples of such methods include methods using differences in solubility such as salt precipitation, and solvent precipitation methods; methods using differences in molecular weight such as dialysis, ultrafiltration, gel filtration and SDS-polyacryl electrophoresis; methods using differences in electrostatic charge (valence) such as ion exchange chromatography; methods using differences in hydrophobicity such as hydrophobic chromatography and reverse phase chromatography; and, methods using differences in isoelectric point such as isoelectric focusing.

In the present invention, as indicated in the Examples below, when this gene was made to express under the control of GAPDH promoter, in a *Saccharomyces cerevisiae* host, high enzyme activity was confirmed within the cell extract. This indicated that it was possible to produce active novel endo-β-N-acetylglucosaminidase in large quantities through the expression of the gene of the present invention in the recombinant.

BRIEF DESCRIPTION OF DRAWINGS

FIG. 3 indicates the entire nucleotide sequence (SEQ ID NO: 1) fo the fragment inserted at the Sal I-Not I site of pZL-Endo which comprises the full length sequence of a novel endo-β-N-acetylglucosaminidase gene.

FIG. 4 indicates the entire nucleotide sequence of the fragment inserted at the Sal I-Not I sites of pZL-Endo which comprises the full length sequence of a novel endo-β-N-acetylglucosaminidase gene. (Continuation of FIG. 3)

FIG. 5 shows the deduced amino acid sequence from novel endo-o-N-acetylglucosaminidase gene and the nucleotide sequence of a DNA (SEQ ID NO: 2) encoding said amino acid (SEQ ID NO: 3) sequence.

FIG. 6 shows the deduced amino acid sequence from novel endo-o-N-acetylglucosaminidase gene and the nucleotide sequence of a DNA (SEQ ID NO: 2) encoding said amino acid sequence (SEQ ID NO: 3). (Continuation of FIG. 5)

FIG. 7 shows the deduced amino acid sequence from novel endo-o-N-acetylglucosaminidase gene and the nucleotide sequence of a DNA (SEQ ID NO: 2) encoding said amino acid sequence (SEQ ID NO: 3). (Continuation of FIG. 6)

FIG. 9 is a chromatography photograph which indicates the expression of novel endo-β-N-acetylglucosaminidase in yeast into which said enzyme gene has been introduced.

BEST MODE FOR CARRYING OUT THE INVENTION

Figure 1:
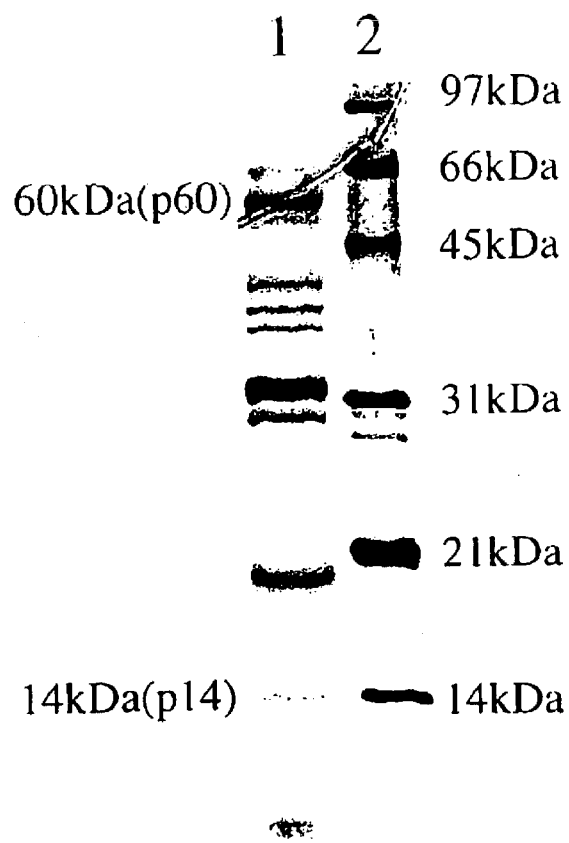
FIG. 1 is an electrophoresis photograph indicating results for purified endo-β-N-acetylglucosaminidase.

Below, the present invention will be described more specifically using examples. It is contemplated, however, that the technical scope of the present invention is not to be limited to these examples. Unless otherwise indicated herein the procedures were performed in accordance with the methods as are described in *Molecular Cloning: A Laboratory Manual* (Sambrook, Maniatis et al, Cold Spring Harbour Laboratory Press (1989)).

EXAMPLE 1

Measurement of Enzyme Activity

Measurement of the activity of endo-β-N-acetylglucosaminidase was performed fundamentally in accordance with the method indicated in S. Kadowaki, et al., *Agric. Biol. Chem.*, 54, 97 (1990). That is, the reaction was performed using dansylated human asialo-transferrin glycopeptide (DNS-GP) as a substrate in a potassium phosphate buffer (pH6.0) at 37° C. and activity measured by thin layer chromatography (TLC) or by HPLC under the following conditions.

Analysis conditions for TLC:
Development phase: HPTLC silica gel 60 (Merck)
Solvent: butanol: acetic acid: water=2:1:1
Detection: detection by fluorescence method
Analysis conditions for HPLC:
Column: TSK-gel ODS80TM (TOSO)
Solvent: 25mM sodium borate buffer (pH 7.5)+11% acetonitrile
Column temperature: 50° C.
Flow rate: 0.5ml/minute
Detector: fluorescence detector Activity was defined such that 1 unit is equivalent to the amount of enzyme required to produce 1 μ mol of dansylated asparagyl acetylglucosamine in one minute under the above described HPLC measurement conditions.

EXAMPLE 2

Culturing *Mucor Hiemalis*

A medium (galactose 2%, yeast extract 3%) 100 ml was placed in a 500 ml Sakaguchi flask, and inoculated with a third to a fifth of a slant of *Mucor heimalis* spore, and culture was performed at 28° C. for 2 days. The microbial cells separated from the culture by suction filtration were used in the preparation of mRNA.

Regarding preparation of the enzyme, the above culture, following cultivation, was transferred to 2 liter of the medium in a 3 liter jar fermenter, and culturing was performed for four days under conditions of 28° C., rotation speed of 300–400 rpm, and aeration volume of 2 liters per minute.

EXAMPLE 3

Purification of Novel Endo-β-N-acetylglucosaminidase

Four liters of the culture (from two batches of cultures performed in 3-liter jar fermenter) obtained in Example 2 was subjected to suction filtration to separate the cells, and concentrated to 200 ml using ultrafiltration. This crude enzyme solution was subjected to ion exchange chromatography (Pharmacia Q Sepharose FF, 500 ml) equilibrated with 10 mM potassium phosphate buffer containing 5mM EDTA. The column was washed with the same buffer solution followed by elution of endo-β-N-acetylglucosaminidase with a linear gradient of 900 ml 0M–0.3M NaCl. Reagents were added to the active fraction such that the final concentrations of 1M ammonium sulfate, 50 mM potassium phosphate containing 5 mM EDTA were attained. The product was subjected to hydrophobic chromatography (TOSO Phenyl-TOYOPEARL 650S 200 ml) equilibrated with the same buffer. The column was washed with this same buffer and then endo-β-N-acetylglucosaminidase was eluted with a linear gradient of 1M–0M ammonium sulfate containing 1 mM EDTA(600 ml).

The obtained eluate was concentrated to 5 ml with ultrafiltration membrane (molecular weight cut-off 13000) then washed and desalted with 10 mM potassium phosphate buffer containing 1 mM EDTA and 0. 15M NaCl (pH7.0). Next, the active fraction was applied to a gel filtration chromatography column (Pharmacia Sephacryl S300) equilibrated with the same buffer solution, and endo-β-N-acetylglucosaminidase was eluted with the same buffer solution.

The active fraction was concentrated with ultrafiltration membrane (molecular weight cutoff 13000) then washed and desalted with 10 mM potassium phosphate containing 1 mM EDTA (pH7.0). Next, the active fraction was subjected to hydroxy apatite chromatography (TOSO TSK-gel HA1000) equilibrated with the same buffer. The column was washed with this same buffer and then endo-β-N-acetylglucosaminidase was eluted with a linear gradient of 0M–0.3M ammonium sulfate containing 1 mM of EDTA (pH7.0)(30 ml).

The active fraction was concentrated with ultrafiltration membrane (molecular weight cut-off 13000) then washed and desalted with a 25mM bis-tris buffer solution adjusted to pH 7.1 with iminodiacetic acid. The active fraction was subjected to isoelectric point chromatography (Pharmacia, MonoP) with equilibrated with the same buffer solution. The column was washed with this same buffer and then endo-β-N-acetylglucosaminidase was eluted with 50 ml of 10% Polybuffer 74 (Pharmacia) adjusted to pH 3.9 with iminodiacetic acid.

The active fraction was concentrated with ultrafiltration membrane (molecular weight cut-off 13000) then washed and desalted with 10 mM potassium phosphate buffer containing 1 mM EDTA (pH7.0). Next, the active fraction was subjected to ion exchange chromatography (Pharmacia, MonoQ). The column was washed with this same buffer and then endo-β-N-acetylglucosaminidase was eluted with a linear gradient of 0M–0.3M NaCl (30 ml).

The active fraction was concentrated with ultrafiltration membrane (molecular weight cut-off 13000) then washed and desalted with 50 mM potassium phosphate buffer containing 1 mM EDTA (pH7.0), to obtain an enzyme sample. It should be noted that each column chromatography was performed using FPLC (Pharmacia).

The mass of the protein was measured using Protein Assay Kit manufactured by BioRad, or by absorbance (280 nm). The molecular weight and isoelectric point of the protein was measured by SDS-PAGE (15–25% gradient), gel filtration chromatography, IEF-PAGE and the like.

From the activity of each of the fractions in two-dimensional electrophoresis by Native-SDSPAGE and IEF-SDSPAGE, and in the above chromatography, and from the results of SDS-PAGE analysis, bands of at least 60 kDa (denoted p60) and 14 kDa (denoted p14) on SDS-PAGE were detected (FIG. 1).

EXAMPLE 4

Determination of a Partial Amino Acid Sequence of Novel Endo-β-N-acetylglucosaminidase Partial amino acid sequence analysis was performed according to the Iwamatsu method (Seikagaku (Biochemistry) 63, 139–143 (1991)). The purified enzyme was suspended in an electrophoresis buffer solution (10% glycerol, 2.5% SDS, 2% 2-mercaptoethanol, 62 mM Tris HCl buffer (pH6.8)), and was subjected to SDS polyacrylamide electrophoresis. After electrophoresis, said enzyme was transferred from the gel to 10 cm by 7 cm PVDF membrane ((ProBlot) Applied Biosystems) by electroblotting. Using ZARUTO Blot Type IIs (Zarutorius) as an electroblotting device, electroblotting was preformed at 160 mA for 1 hour. After transfer, the portion of the membrane onto which the said enzyme was transferred was cut out and part of this portion was directly analyzed with a gas phase protein sequencer whereby the N-terminal amino acid sequence was determined. Further, the remaining membrane was soaked in 300 µl of a reducing buffer solution (8M guanidine-HCl, 0.5M Tris-HCl buffer (pH8.5), 0.3% EDTA, 2% acetonitrile), 1 mg of ditiothreitol (DTT) was added, and reduction was performed for about 1 hour at 25° C. in the presence of argon. To this, 3.0 mg of monoiodoacetic acid dissolved in 10 µl of 0.5N sodium hydroxide solution was added and was stirred for 20 minutes under darkened conditions. PVDF membrane was taken out, and after thorough enough washing with 2% acetonitrile, it was soaked in 100 mM acetic acid containing 0.5% polyvinylpyrrolidone-40, and allowed to stand for 30 minutes. Afterward, the PVDF membrane was washed thoroughly with water. A 1 mm square was cut from the membrane and soaked with a digestion buffer (8% acetonitrile, 90 mM Tris-HCl buffer pH 9.0) and 1 pmol of Acromobacter protease I (Wako Pure Chemicals Industries) was added thereto. The enzyme was then digested for 15 hours at room temperature. The digestion product was separated by reversed phase high performance liquid chromatography on C18 column (Wakosil AR II C18 300 Å 2.0×150 mm(Wako Pure Chemicals Industries)), and seven peptide fragments were obtained in respect of each subunit.

As elution solvents for the peptides, solvent A (0.05% trifluoroacetic acid) and solvent B (2-propanol/acetonitrile solution 7:3, containing 0.02% trifluoroacetic acid) were used, and the elution was performed for 40 minutes with a linear concentration gradient from 2 to 50% of solvent B, at a rate of 0.25 mL/min.

Amino acid sequences of fragmented peptides obtained from the novel endo-β-N-acetylglucosaminidase candidate protein were analyzed. Fragments derived from p60 and fragments derived from p14, were denoted as p60-AP and p14-AP, respectively. Sequencing of the obtained fragmented peptides was carried out using a gas phase protein sequencer PPSO-10 (Shimadzu) by the Edman degradation method in accordance with the manual.

The obtained partial amino acid sequences are indicated in Table 1.

TABLE 1

Partial amino acid sequence of endo-β-N-acetylglucosaminidase candidate protein

| p60 | | |
|---|---|---|
| p60-AP-5 | PSLQLQPDDK | (SEQ ID NO: 17) |
| p60-AP-6 | (K) SYRNPEIYPtDQNIK | (SEQ ID NO: 18) |
| p60-AP-8 | (K) FNVSSVALQPRVK | (SEQ ID NO: 19) |
| p60-AP-9 | (K) MDRLFLCGgK S | (SEQ ID NO: 20) |
| p60-AP-11 | (K) GQRFNHREShDVETEI mal p lllt | (SEQ ID NO: 21) |
| p14 | | |
| p14-AP-1 | (K) EGYISSSGSIDLSLN | (SEQ ID NO: 22) |

In the amino acid sequence described in Table 1, amino acids indicated by lower case letters of the alphabet are undetermined amino acids within the amino acid sequence.

Since Acromobacter protease I, used on the partial amino acid sequence, specifically cleaves on the carboxyl side of a lysine residue, K (lysine) has been written in brackets on the N-terminus side of the sequences below.

Since the p60-AP-5 was found to be the N-terminus amino acid sequence, K (Lysinse) in brackets was removed.

In respect of the Acromobacter protease I digestion products of p60 and p14, molecular weight analysis was also performed with on-line mass analyzer (PE Sciex API-III), combined with reverse phase high performance liquid chromatography (Hitachi L6200) on C-18 column (GL Science Inertsil ODS-3 0.5×40mm). The results of analysis are shown in Table 2.

TABLE 2

Results of /Lys-C digest product on the 60 kDa peptide (p60) and the 14 kDa peptide (p14) by LC/MS analysis

|  | Measured Value | Ideal Value | Error Margin | Corresponding Sequence | SEQ ID NO: |
|---|---|---|---|---|---|
| p60 |  |  |  |  |  |
| AP-1: | 950.50 | 950.47 | +0.03 | (K)NIQGNNYK | 23 |
| AP-2: | 1160.50 | 1160.56 | −0.06 | (K)YSDYPPPPPK | 24 |
| AP-3: | 733.25 | 733.41 | −0.16 | (K)LSLDASK | 25 |
| AP-4: | 1838.50 | 1837.91 | +0.59 | (K)SYRNPEIYPTDQNIK | 18 |
| AP-5: | 1141.00 | 1140.59 | +0.41 | ( )PSLQLQPDDK . . . p60 N-terminus | 17 |
|  | 1157.50 | 1556.75 | +0.75 | (K)NTDGIFLNYWWK | 26 |
| AP-6: | 1774.75 | 1774.94 | −0.19 | (K)GB*SLRYIYRTLLMK | 27 |
| AP-7: | 701.50 | 701.39 | +0.11 | (K)LTVAB*H . . . p60 C-terminus | 28 |
|  | 1544.50 | 1543.79 | +0.71 | (K)PQLLLTHDMAGGYK | 29 |
|  | 1621.00 | 1620.73 | +0.27 | (K)SMNELRDWTPDEK | 30 |
| AP-8: | 1444.75 | 1444.83 | −0.08 | (K)FNVSSVALQPRVK | 19 |
| AP-9: | 945.75 | 945.58 | +0.17 | (K)LAPVSFALK | 31 |
|  | 2655.00 | 2655.33 | −0.33 | (K)GQRFNHRESHDVETEISIPLYK | 32 |
| AP-10: | 2206.75 | 2206.11 | +0.64 | (K)ITSSLDB*DHGAFLGGTSLIIK | 33 |
| AP-11: | 2335.00 | 2335.16 | −0.16 | (K)NELFFKNTDGIFLNYWWK | 34 |
| p14 |  |  |  |  |  |
| AP-1: | 888.75 | 888.45 | +0.30 | (K)IVIEAVNK | 35 |
| AP-2: | 1392.50 | 1392.76 | −0.26 | ( )SSRIIQDLFWK . . . p14 N-terminus | 36 |
| AP-3: | 1541.50 | 1541.73 | −0.23 | (K)EGYISSSGSIDLSLN . . . p14 C-terminus | 22 |
|  | 1608.50 | 1608.84 | −0.34 | (K)TDSSRIIQDLFWK | 37 |

*B represents cysteine, carboxymethyl.

In Table 2, the fragment having a measured value of 701.50 in respect of mass (M+H+) is p60-AP-7, and the fragment having a measured value of 1541.50 is nearly identical to the molecular weight of p14-AP-3, and it was found that the amino acid at this C-terminus was not K (1ysine). Regarding the fragments digested with Acromobacter protease I, since, due to the substrate specificity of this enzyme, fragments other than C-terminus fragment of the subunit itself, will have a C-terminus amino acid residue that is lysine (K), it is clear that these fragmented peptides were the C-terminus fragments of the subunits p60 and p14.

A homology search on the determined p60 and p14 partial amino acid sequences using the protein database BLASTP indicated that the obtained sequences were novel. From the above results, gene cloning of p60 and p14 was performed selecting the p60 and p14 as endo-β-N-acetylglucosaminidase candidates.

EXAMPLE 5

Construction of a *Mucor hiemalis* Strain cDNA Library

Firstly, total RNA was extracted from 5 g of the microorganisms obtained in Example 2 using ISOGEN (Nippon Gene, Inc.). From the extracted total RNA, mRNA was purified using an mRNA Purification Kit (Pharmacia Biotech). cDNA was synthesized from the mRNA using a SuperScript™ Lambda System for cDNA Synthesis and λ Cloning Kit (GIBCO BRL), and then ligated to a Sal I adapter, and finally linked (or ligated) to λ ZipLox™ Sal I-Not I Arms (GIBCO BRL). Packaging was performed using Gigapack III Gold Packaging Extract (Stratagene), for infection of *E.coli* Y1090 strain thereby constructing the cDNA library.

EXAMPLE 6

Cloning of Novel Endo-β- N-acetylglucosaminidase cDNA

PCR primers were designed based on the partial amino acid sequences p60AP-5, p60-AP-6, p60-AP-11. These sequences are indicated below. The symbols used herein are all based on IUPAC-IUB.

p60-AP-5
p60-AP-5F 5' CARTTRCARCCNGAYGAYAA 3' (sense primer) (SEQ ID NO: 5)
p60-AP-6
p60-AP-6F 5' CCHACNGAYCARAAYATYAA 3' (sense primer) (SEQ ID NO: 7)
p60-AP-6R 3' GGDTGNCTRGTYTTRTARTT 5' (antisense primer) (SEQ ID NO: 8)
p60-AP-11
p60-AP-11R 3' TTYCCDGTYGCDAARTTRGT 5' (antisense primer) (SEQ ID NO: 10)

Genomic DNA was purified from *Mucor hiemalis* culture mass by the phenol method and when genomic PCR (30 seconds at 94° C., 1 minute at 55° C., 1 minute at 72° C., 30 cycles) was performed, specific amplified bands were confirmed. Regarding p60, with a combination of p60AP-5F and p60-AP-11R primers, a PCR fragment of 1.7 kb, with combination of p60-AP-5F and p60-AP-6R, a PCR fragment of 1.5kb, and with a combination of p60-AP-6F and p60-AP-11R primers, a PCR fragment of 0.2 kb was obtained. Regarding this fragment, subcloning into pCR-Script Amp was performed using a pCR-Script cloning kit (Stratagene). It was predicted from analysis by restriction enzyme digestion, that the amplification fragment of p60-AP-5F and p60-AP-11R included the amplification fragments of p60-AP-5F and p60-AP-6R, and p60-AP6F and p60-AP-11R. Thus, the nucleotide sequence of the amplification fragment of p60-AP-5F and p60-AP-11R was determined using PRISM Ready Reaction kit (Applied Biosystems) and PRISM 377 DNA sequencer (Applied Biosystems). Gene analysis was performed using DNASIS (Hitachi Software Engineering Co., Ltd.) etc.

As a result, the amplification fragment of p60-AP-5F and p60AP-11R included the determined other partial amino acid sequence. Therefore, it was determined that this fragment was a part of the p60 gene. Thus, new DNA primers were constructed based on the inside sequence of the PCR amplification fragment, and RT-PCR was then performed (under the same conditions as genomic PCR), using Access RT-PCR System (Promega) and with the mRNA obtained in Example 5 as a template. The sequences of the newly constructed DNA primers are as follows:

p60AP-5NF 5' CACTTAAGTCTATGAATGAG 3' (sense primer) (SEQ ID NO: 13)

p60AP-6NR 3' CGATAGCTTTAGGTCTCTAA 5' (antisense primer) (SEQ ID NO: 14)

As a result, a fragment of approximately 1.2 kb was amplified. Upon sequencing the amplified fragment it was found that a fragment not including introns had been obtained. Therefore, CDNA cloning was performed using this fragment as a probe. Labeling was performed with $\alpha$-$^{32}$P dCTP (100 TBq/mmol) using Megaprime DNA labeling systems (Amersham).

Figure 2:
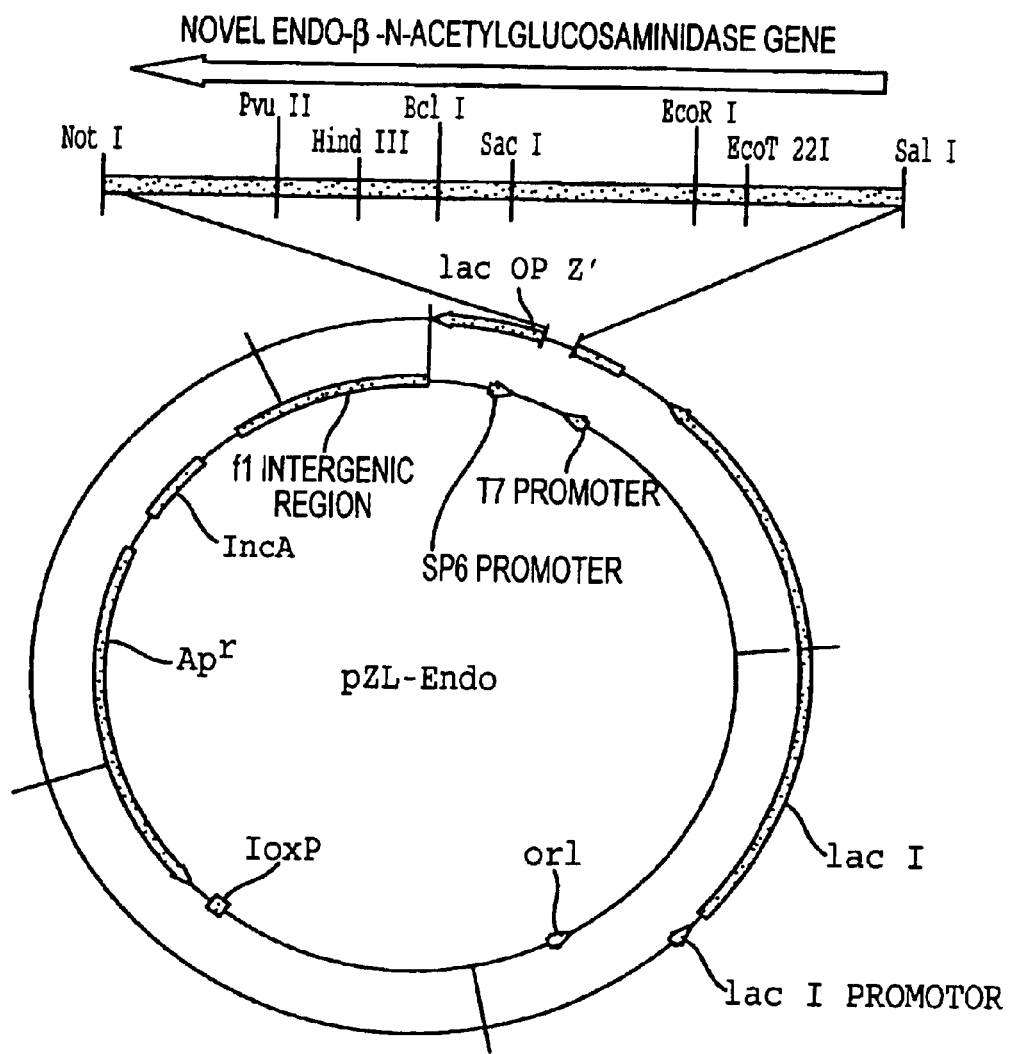
FIG. 2 is a restriction enzyme map of pZL-Endo which comprises the full length sequence of a novel endo-β-N-acetylglucosaminidase gene.

The full-length gene was obtained from the cDNA library, obtained in Example 5, by plaque hybridization. As a result, 5 positive clones were obtained from 200,000 plaques. Of these, 4 clones were subjected to secondary screening thereby obtaining a single plaque. Further, E.coli DH10B was infected with phage fluid obtained from the plaque, and a plasmid derived from pZL1 was recovered from the phage. Restriction enzyme analysis was performed in respect of these clones, and nucleotide sequence analysis of the clone comprising the longest upstream region was performed. This plasmid was named pZL-Endo. (FIG. 2)

The nucleotide sequence of the inserted Sal I-Not I fragment of about 2.3 kb was determined. In other words, the restricted fragments were subcloned into pBluescript II KS+(Stratagene) or pUC118 (Takara Shuzo), and by producing a continuous deletion mutant using exonuclease III and mung bean nuclease, a plasmid having a variety of deletion mutations was constructed, and the sequence of a Sal I-Not I fragment consisting of 2370 bp was determined using a DNA sequencer. (FIGS. 3–4, SEQ ID NO: 1)

Analysis of the predicted region of the structural gene was performed and it was found that there existed an open reading frame encoding an amino acid sequence consisting from 744 amino acid residues (deduced molecular weight 85 kDa, FIGS. 5–7, SEQ ID NO: 2), and this amino acid sequence comprised all of the determined partial amino acid sequences of p60 and p14. Since the amino acid next to p60-AP-5 on the N-terminus side was not lysine but methionine, it was confirmed that ATG encoding this methionine was the start codon for translation. It had therefore been clarified that the N-terminus of the enzyme of the present invention was proline.

On the other hand, as with the result of qualitative analysis, it was found that p14-AP-3 was the C-terminus of the protein encoded by the gene of the present invention. Further, together with the results of mass analysis, it was predicted that at least one type of p14 N-terminus was serine, the amino acid at position 628 in the amino acid sequence indicated in SEQ ID NO: 2.

From the above, it was clear that the 5' region of the gene of the present invention encodes p60, and the 3' region encodes p14. Since the N-terminal signal sequence could not be found in the amino acid sequence, the enzyme of the present invention is thought to be an intracellular protein. However, since there exists a plurality of bands in FIG. 1, the enzyme of the present invention is thought to be affected by action of a protease due to the lysis of the cell.

EXAMPLE 7

Construction of the Endo-β-N-acetylglucosaminidase Gene Expression Vector

In this Example, an expression vector for *Saccharomyces cerevisiae*, complementary to a TRP1 gene, including an endo-β-N-acetylglucosaminidase gene and a GAPDH gene promoter-PGK terminator was constructed.

To obtain the open reading frame encoding the 744 amino acids confirmed in Example 3, DNA primers based on DNA sequences equivalent to the amino acid sequences of the N-terminus and C-terminus to which a Not I site had been added at both termini, were synthesized and PCR was performed with pZL-Endo as a template thereby obtaining an amplified fragment. The following are the sequences of the sense and antisense primers:

Endo-Not-F (Sense Primer)

5' GGGGCGGCCGCTTTTTATTTACAT-AAATATGCCTTCACTTC 3' (SEQ ID NO: 15)

Endo-Not-R (Antisense Primer)

5' CCCGCGGCCGCCTAGTTTAATGA-CAAATCTATGCTACC 3' (SEQ ID NO: 16)

After separation by agarose gel electrophoresis, the amplified fragment was recovered and purified using Prep-A-Gene DNA Purification System (Bio-Rad). Further, after digestion of this fragment with Not I, it was purified and inserted into the Not I of pBluescript II KS+ thereby producing pBlue-Endo-Not.

Since the novel endo-β-N-acetylglucosaminidase gene is the gene derived from mold, it was thought that expression in yeast was suitable. An expression plasmid for *Saccharomyces cerevisiae* with trp1 gene as a selective marker, said trp 1 gene comprising a *Saccharomyces cerevisiae* glyceraldehyde-3-phosphate dehydrogenase gene (GAPDH) promoter, a 3-phophoglycerate kinase (PGK) gene terminator, and a tryptophan synthesis gene TRP1 gene, was constructed with expression vector pG-3 (Methods in Enzymology Vol. 194 p. 389). Said pG-3-Not was constructed by digesting pG-3 with BamHI, blunt-ending by Klenow processing followed by addition of a Not I linker.

Figure 8:
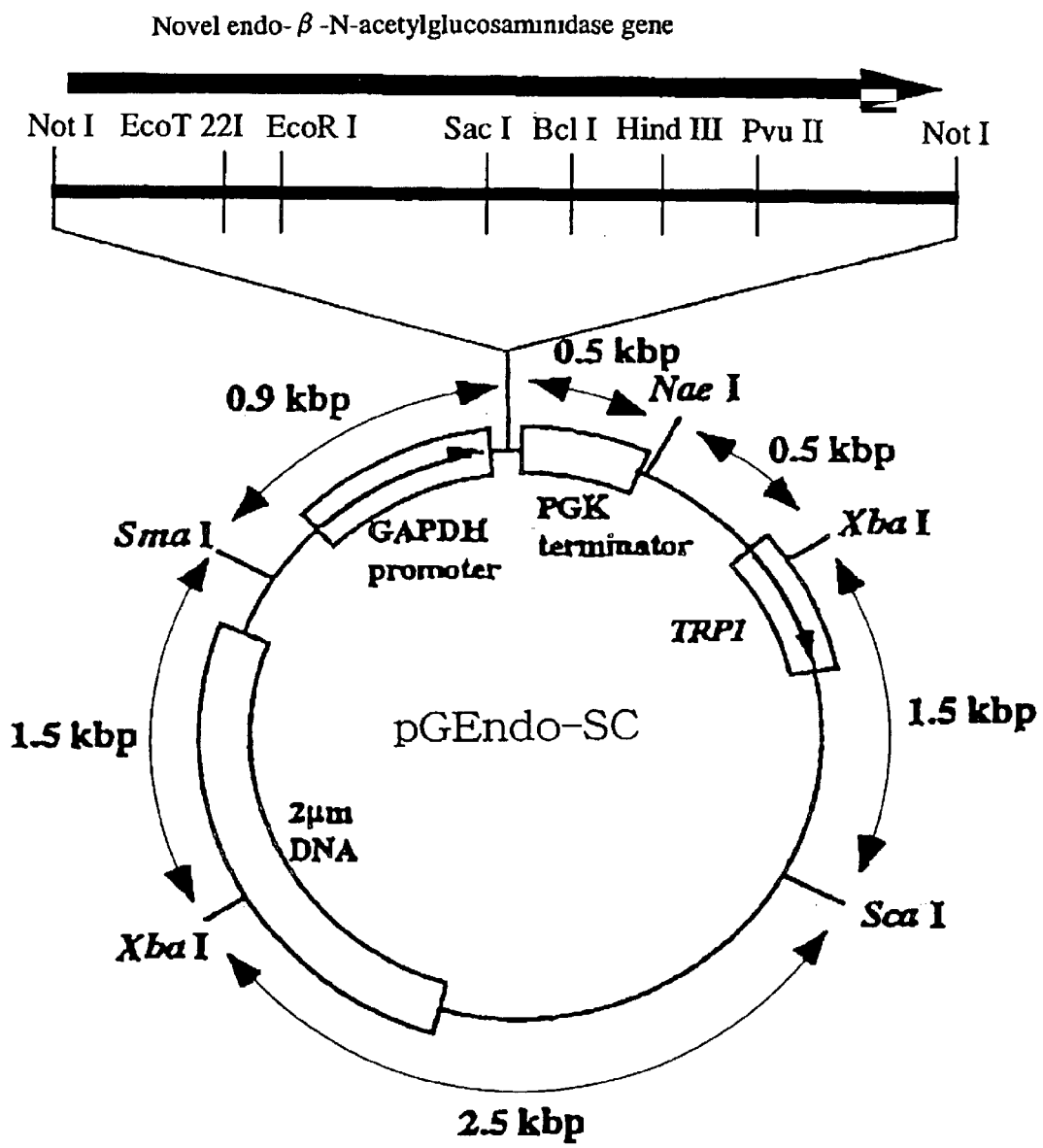
FIG. 8 shows the structure of expression vector pGEndo-SC, which comprises a novel endo-β-N-acetylglucosaminidase gene for use in *Saccharomyces cerevisiae*.

The above-mentioned pBlue-Endo-Not was digested with Not I and an insertion fragment of approximately 2.3 kb separated and purified by agarose gel electrophoresis. This fragment was inserted at the Not I site of pG-3-Not thereby constructing pGEndo-SC. (FIG. 8)

EXAMPLE 8

Expression of Novel Endo-β-N-acetylglucosaminidase in *Saccharomyces cerevisiae*

A pep4 gene disrupted strain of the yeast *Saccharomyces cerevisiae* YPH500 strain (Stratagene) was used as a host. A pep4 gene disrupted strain was produced by the method of Sikorski, R. S. and Hieter, P (Genetics Vol. 122 19–27 (1989)). The said strain was transformed with 10 μg of pGEndo-SC. Transformation was performed by the lithium acetate method (see WO95/32289) and transformants were selected on a culture plate not including tryptophan (yeast nitrogen base 0.67%, casamino acid 0.5%, glucose 1%).

Confirmation of the activity of intracellular novel endo-β-N-acetylglucosamrinidase was performed in respect of the transformants. For the transformed cells cultured for 2 days at 30° C. in a 5 mL YPD medium (yeast extract 1%, polypeptone 2%, glucose 2%), centrifugation was performed at 1500 g for 5 minutes at 4° C., thereby separating the supernatant and the cell mass. The cell mass was washed with distilled water. Ten microliters of a mixture of 50 mM potassium sulfate buffer (pH 6.0) and 5 mM EDTA was added to the cell mass and suspended well. Further, 50 mg of glass beads was added and after vigorous stirring, centrifuged, and the supernatant taken was as the cell extract.

Measurement of activity was performed by TLC or HPLC using DNS-GP as a substrate. Results with TLC are indicated in FIG. 9. As with the sample reacted with the enzyme purified from the supernatant of the *Mucor hiemalis* culture, a peak identical with the dansylated asparagyl acetylglucosamine (DNS-Asn-GlcNAc) was obtained from the pGEndo-SC product. On the other hand, no peak corresponding to DNS-Asn-GlcNAc was detected from the culture supernatant of the negative control strain transformed with pG-3-Not. The pGEndo-SC cell extract was concentrated by a factor of ten, desalted, reacted with DNS-GP and the peak corresponding to DNS-Asn-GlcNAc was fractionated using HPLC under the above-mentioned conditions. The fractionated samples were concentrated with an evaporator, and mass spectrometry analysis was performed thereon. As a result, it was confirmed that the mass spectrometry results matched with the DNS-Asn-GlcNAc results. Thus it was apparent that the gene product encoded by the pGEndo-SC insertion fragment was a novel endo-β-N-acetylglucosaminidase.

Table 3 indicates the activity (product amount) per liter of the culture of the novel endo-β-N-acetylglucosaminidase of this invention. This activity was 48 times the value for *Mucor hiemalis*.

TABLE 3

Novel endo-β-N-acetylglucosaminidase activity

| | Activity (Unit/Liter) |
|---|---|
| *M. hiemalis* culture supernatant | 0.9 |
| Culture fluid of *S. cerevisiae* into which novel endo-β-N-acetylglucosaminidase gene was introduced* | 43.2 |

*After cell collection from the culture, the cells were disrupted with glass beads. After separation of the supernatant using a centrifuge, the activity of the supernatant was measured, and the activity per culture volume was calculated from this value.

This specification incorporates the content described in the specification and/or the drawings of Japanese Patent Application No. 10-141717 which is the application upon which priority for the present application is based.

All publications, patents and patent applications cited herein are incorporated herein by reference in their entirety.

Industrial Applicability

The present invention provides an endo-β-N-acetylglucosaminidase, an endo-β-N-acetylglucosaminidase gene, a recombinant plasmid which comprises said gene, an organism transformed with said plasmid, and a method of producing endo-β-N-acetylglucosaminidase.

By introducing a vector which comprises the gene of the present invention into a host, and causing the gene to be expressed, endo-β-N-acetylglucosaminidase can be produced efficiently and in large quantities.

The enzyme of the present invention is an industrially important enzyme in the analysis and assay of sugar chains and the modification of sugar chains. The transformants obtained by the present invention produce the subject enzyme in large quantities and make a large contribution to industries that employ these enzymes.

Free Text of Sequence Listing

SEQ ID NO: 4: A partial amino acid sequence of endo-β-N-acetylglucosaminidase
SEQ ID NO: 5: An oligonucleotide designed from a partial amino acid sequence of endo-β-N-acetylglucosaminidase
SEQ ID NO: 5: n indicates a, g, c, or t (Location: 12)
SEQ ID NO: 6: A partial amino acid sequence of endo-β-N-acetylglucosaminidase
SEQ ID NO: 7: An oligonucleotide designed from a partial amino acid sequence of endo-β-N-acetylglucosaminidase
SEQ ID NO: 7: n indicates a, g, c, or t (Location: 6)
SEQ ID NO: 8: An oligonucleotide designed from a partial amino acid sequence of endo-β-N-acetylglucosaminidase
SEQ ID NO: 8: n indicates a, g, c, or t (Location: 15)
SEQ ID NO: 9: A partial amino acid sequence of endo-β-N-acetylglucosaminidase
SEQ ID NO: 10: An oligonucleotide designed from a partial amino acid sequence of endo-β-N-acetylglucosaminidase
SEQ ID NO: 11: An oligonucleotide sequence of the 5' terminal region of an endo-β-N-acetylglucosaminidase gene
SEQ ID NO: 12: An oligonucleotide sequence of the 3' terminal region of an endo-β-N-acetylglucosaminidase gene
SEQ ID NO: 13: An oligonucleotide designed from the nucleotide sequence of an endo-β-N-acetylglucosaminidase gene
SEQ ID NO: 14: An oligonucleotide designed from the nucleotide sequence of an endo-β-N-acetylglucosaminidase gene
SEQ ID NO: 15: An oligonucleotide designed from the nucleotide sequence of an endo-β-N-acetylglucosaminidase gene
SEQ ID NO: 16: An oligonucleotide -designed from the nucleotide sequence of an endo-β-N-acetylglucosaminidase gene
SEQ ID NO: 20: Xaa indicates Met or Ser (Location: 2)
SEQ ID NO: 21: Xaa indicates Gly or Met (Location: 2)
SEQ ID NO: 21: Xaa indicates Gln or Ala (Location: 3)
SEQ ID NO: 21: Xaa indicates Arg or Leu (Location: 4)
SEQ ID NO: 21: Xaa indicates Asn or Pro (Location: 6)
SEQ ID NO: 21: Xaa indicates Arg or Leu (Location: 8)
SEQ ID NO: 21: Xaa indicates Glu or Leu (Location: 9)
SEQ ID NO: 21: Xaa indicates Ser or Leu (Location: 10)
SEQ ID NO: 21: Xaa indicates His or Thr (Location: 11)
SEQ ID NO: 27: carboxymethylcystein (Location: 3)
SEQ ID NO: 28: carboxymethylcystein (Location: 6)
SEQ I) NO: 33: carboxymethylcystein (Location: 8)

What is claimed is:

1. An isolated endo-β-N-acetylglucosaminidase gene encoding:
   (a) a protein comprising the amino acid sequence represented by SEQ ID NO: 3; or
   (b) a protein comprising an amino acid sequence derived from the amino acid sequence represented by SEQ ID NO: 3 by deletion, substitution, insertion, or addition of 1–10 amino acids and having the activity endo-β-N-acetylglucosaminidase.

2. An isolated gene comprising the following DNA:
   (a) a DNA consisting of a nucleotide sequence represented by SEQ ID NO: 2.

3. The gene according to claim 1, wherein the gene is isolated from a microorganism belonging to the genus *Mucor*.

4. The gene according to claim 3, wherein the microorganism belonging to the genus *Mucor* is *Mucor hiemalis*.

5. A recombinant vector which comprises the gene according to claim 1.

6. A transformant which comprises the recombinant vector of claim 5.

7. A method of using the transformant of claim 6 to produce endo-β-N-acetylglucosaminidase comprising culturing the transformant of claim 6 and collecting endo-β-N-acetylglucosaminidase from the culture product.

8. The gene according to claim 2, wherein the gene is isolated from a microorganism belonging to the genus *Mucor*.

9. A recombinant vector which comprises the gene according to claim 2.

10. A recombinant vector which comprises the gene according to claim 3.

11. A recombinant vector which comprises the gene according to claim 4.

12. A transformant which comprises the recombinant vector of claim 9.

* * * * *